United States Patent [19]
Corey et al.

[11] Patent Number: 5,191,073
[45] Date of Patent: Mar. 2, 1993

[54] CHROMOGENIC MEROCYANINE ENZYME SUBSTRATES

[75] Inventors: Paul F. Corey; M. Teresa Yip, both of Elkhart, Ind.

[73] Assignee: Miles Inc., Elkhart, Ind.

[21] Appl. No.: 841,791

[22] Filed: Feb. 26, 1992

Related U.S. Application Data

[62] Division of Ser. No. 310,060, Feb. 13, 1989, Pat. No. 5,122,602.

[51] Int. Cl.$^5$ .................. C07H 17/04; C07H 5/06; C12Q 1/54; G01N 33/58
[52] U.S. Cl. .................. 536/17.2; 536/4.1; 536/17.3; 536/17.7; 536/17.5; 435/18; 435/14; 435/19; 435/21
[58] Field of Search ............. 536/17.2, 4.1, 17.3, 536/17.5, 17.7; 435/14, 18, 19, 21

[56] References Cited

U.S. PATENT DOCUMENTS

| | | | |
|---|---|---|---|
| 4,536,572 | 8/1985 | Kim et al. | 536/4.1 |
| 4,668,622 | 5/1987 | Kuhr et al. | 536/4.1 |
| 4,754,025 | 6/1988 | Makise et al. | 536/17.2 |
| 4,760,135 | 7/1988 | Diedrich et al. | 536/17.2 |
| 4,760,136 | 7/1988 | Mori et al. | 536/17.2 |

FOREIGN PATENT DOCUMENTS 0047470 1/1981 European Pat. Off. .

OTHER PUBLICATIONS

Richardson et al.; "Chromogenic Substituted Arylethene Derivatives as Substrates for Hydrolytic Enzyme Assays"; Chemical Abstracts; (112) (11): 94609m.

*Primary Examiner*—Ronald W. Griffin
*Assistant Examiner*—Louise N. Leary
*Attorney, Agent, or Firm*—Jerome L. Jeffers

[57] ABSTRACT

Chromogenic merocyanine enzyme substrate compounds of the general formula:

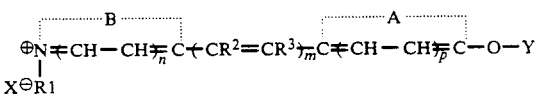

where Y is an enzymatically-cleavable group such as a radical of a sugar, carboxylic acid, amino acid, peptide, phosphoric acid, or sulfuric acid; A and B represent residues that complete 5- or 6-membered ring systems; $R^1$ is substituted or unsubstituted alkyl; $R^2$ and $R^3$, independently, are hydrogen or lower alkyl; m, n, and p, which can be different, are integers from 0 through 3 provided that m+n+p must be at least 2; and X is an appropriate counterion (anion).

15 Claims, 9 Drawing Sheets

CHROMOGENIC MEROCYANINE ENZYME SUBSTRATES

This is a division of application Ser. No. 310,060, filed on Feb. 13, 1989, now U.S. Pat. No. 5,122,602.

BACKGROUND OF THE INVENTION

The present invention relates to chromogenic compounds which are useful as optical indicator compounds in analytical test systems. In particular, the present invention relates to novel chromogenic enzyme substrate compounds and their use in analytical test systems for the detection of enzymes in a liquid test sample.

The determination of enzymes is important in a variety of fields such as biochemical research, environmental and industrial testing, and medical diagnostics. The quantitation of enzyme levels in body fluids such as serum and plasma provides very useful information to the physician in diagnosing diseased states and their treatment. In addition to being analytes of interest in biological fluids, enzymes can also serve as detection reagents in a variety of analytical systems such as immunoassays and nucleic acid hybridization techniques. In such systems, enzymes are useful directly or indirectly as labels to monitor the extent of antigen-antibody binding or nucleic acid hybridization that occurs.

Accordingly, the desire to detect enzyme analytes and to use enzyme labels as a diagnostic tool in various analytical test systems has given rise to the development of optical indicator compounds for use in the detection and measurement of the activity of such enzymes. Typically, such known optical indicator compounds comprise a detectable chemical group, such as a fluorogen or a chromogen, which has been derivatized with an enzyme cleavable substrate group specific for the enzyme of interest. Such optical indicator compounds exhibit an optical signal which is different from the optical signal which is provided by the cleaved native form of the fluorogen or chromogen. In principle, the enzyme cleaves the indicator compound to liberate the fluorogen or chromogen in the form of a distinctly fluorescent or colored product to provide a change in fluorescence or color which is proportional to the amount of enzyme present which, in turn, can be correlated to the amount of analyte present in a liquid test sample.

In particular, the detection and/or determination of hydrolases, i.e., enzymes which catalyse hydrolysis reactions of esters, glycosidic bonds, peptide bonds, other carbon-nitrogen bonds, and acid anhydrides [see Lehninger, Biochemistry (Worth Publishers, Inc, New York, N.Y., 1970) p. 148], is of interest in the diagnosis and monitoring of various diseases such as, for example, the determination of amylase and lipase in the diagnosis of pancreatic disfunction [see Kaplan and Pesce, Clinical Chemistry—Theory, Analysis and Correlation (C. V. Mosby Co., St. Louis, Mo., 1984) Chapter 56], determination of N-acetylglucosaminidase (NAG) as an indicator of renal disease [see Price, Curr. Probl. Clin. Biochem. 9, 150 (1979)] and detection of esterase as an indicator for leukocytes [see Skjold, Clin. Chem. 31, 993 (1985)].

Enzymes have also gained importance in the diagnostic as well as the biotechnology fields. For example, alkaline phosphatase and β-D-galactosidase have found increasing use as indicator enzymes for enzyme immunoassays [see Annals of Clinical Biochemistry 16, 221–40 (1979)]. Accordingly, the use of enzymes such as glycosidases, particularly β-D-galactosidase, as indicator enzyme labels in analytical test systems has given rise to the development of substrate glycosides such as phenyl-β-D-galactoside, o-nitrophenyl-β-D-galactoside and p-nitrophenyl-β-D-galactoside [see Biochem. Z., Vol. 33, p. 209 (1960)] which are hydrolysed by β-D-galactosidase to liberate the phenols which are determined photometrically in the ultraviolet range, or the nitrophenols which are determined in the shortwave visible range, respectively. A few other examples are the chromogenic resorufin derivatives of European Patent application No. 156,347, and the chromogenic acridinone derivatives of European Patent Application No. 270,946.

The use of β-D-galactosides has also been described in conjunction with histochemical investigations, such as the naphthyl-β-D-galactosides described in Histochemie, Vol. 35, p. 199 and Vol. 37, p. 89 (1973), and the 6-bromo-α-naphthyl derivatives thereof described in J. Biol. Chem., Vol. 195, p. 239 (1952). According to such test systems, the naphthols which are liberated upon the interaction of the galactoside with the enzyme are reacted with various diazonium salts to yield the respective azo-dyes which can then be visualized.

There continues to be a need for new compounds having desirable combinations of chromogenic substrate properties such as extinction coefficient, absorbance maxima, water solubility, color shift, and turnover rate.

Merocyanine dyes have previously been used as analytical reagents, although not as chromogenic enzyme substrates. European Patent Application No. 47470 describes the use of cyanine and merocyanine dyes as labels for antibodies or antigens in an immunochemical assay. The labeled antigen or antibody is subjected to an immune reaction and contacted with a silver halide which is then exposed to light and developed. The resulting optical density is measured. PCT Publication No. 86-06374 describes a conjugate of a highly fluorescent merocyanine dye with a biologically active moiety useful in diagnostic assays. The application uses dye-labeled antibodies to measure analytes in a test sample. Kiciak [Roczniki Chemii 37,225(1963)] describes the preparation of a merocyanine acetate ester but gives no suggestion that it might function as a chromogenic enzyme substrate.

SUMMARY OF THE INVENTION

The present invention provides novel chromogenic merocyanine enzyme substrate compounds of the general formula (A):

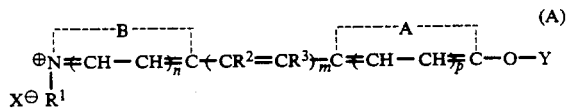

where Y represents an enzymatically cleavable group that is selected to confer specificity for the corresponding enzyme of analytical interest. Further, A represents a nonmetallic atomic group or residue which completes a 5- or 6-membered carbocyclic or heterocyclic ring or a fused ring system consisting of 5- and/or 6-membered heterocyclic or carbocyclic rings; B represents a nonmetallic atomic group or residue which completes a 5- or 6-membered N-containing heterocyclic ring or a fused ring system consisting of 5- and/or 6-membered heterocyclic or carbocyclic rings; $R^1$ is alkyl or aryl; $R^2$ and $R^3$, which may be the same or different, are hydrogen or lower alkyl; m, n, and p, which may be the same or different, are integers from 0 through 3 provided that $m+n+p$ is at least 2; and X is a counterion (anion). The ring system formed with the group A in the formula is referred to herein as the acidic nucleus, and that formed with the group B as the basic nucleus.

DESCRIPTION OF THE PREFERRED EMBODIMENTS

Figure 1:
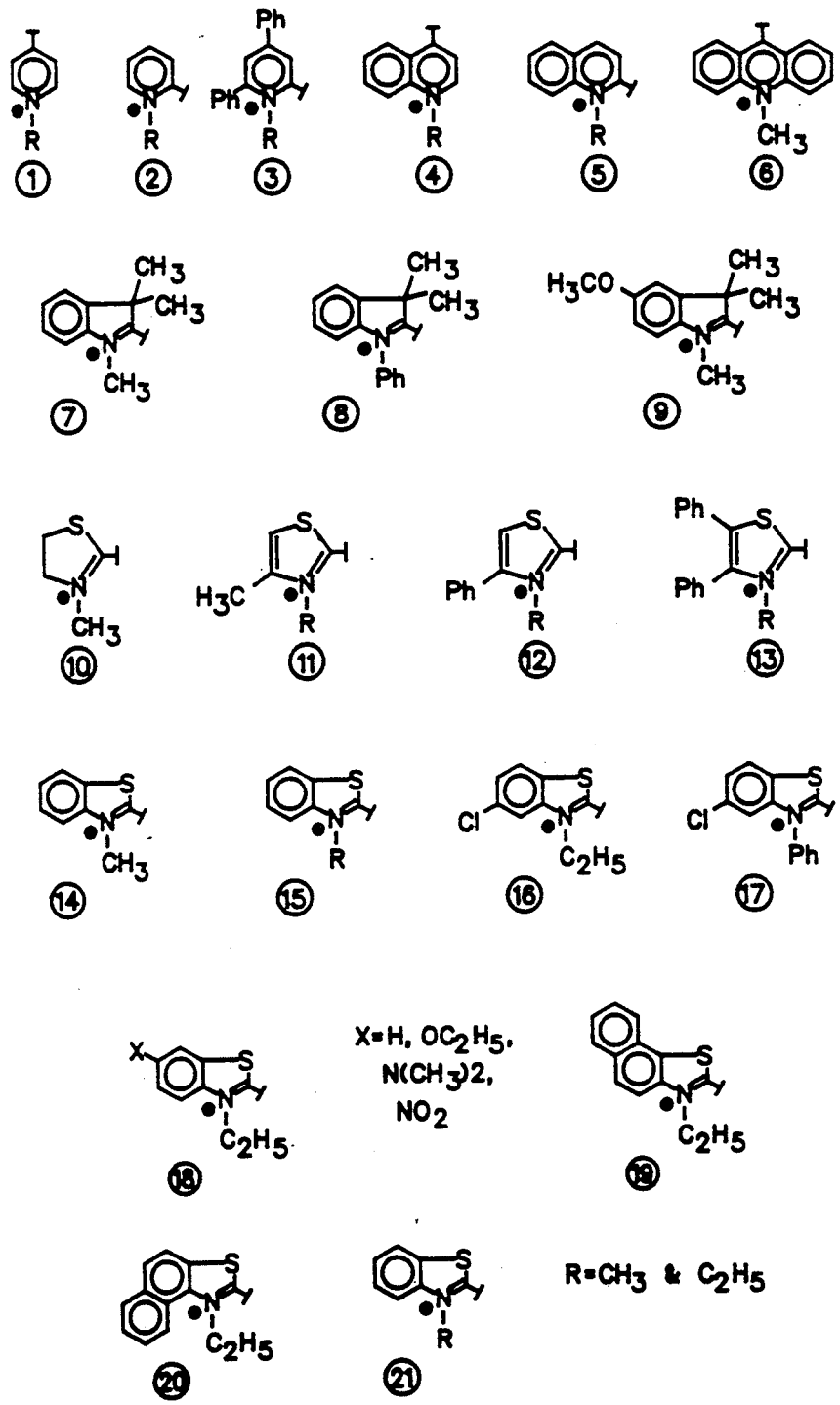
FIGS. 1 and 1a are tables of some representative basic and acidic nuclei that can form merocyanines.
Figure 1A:
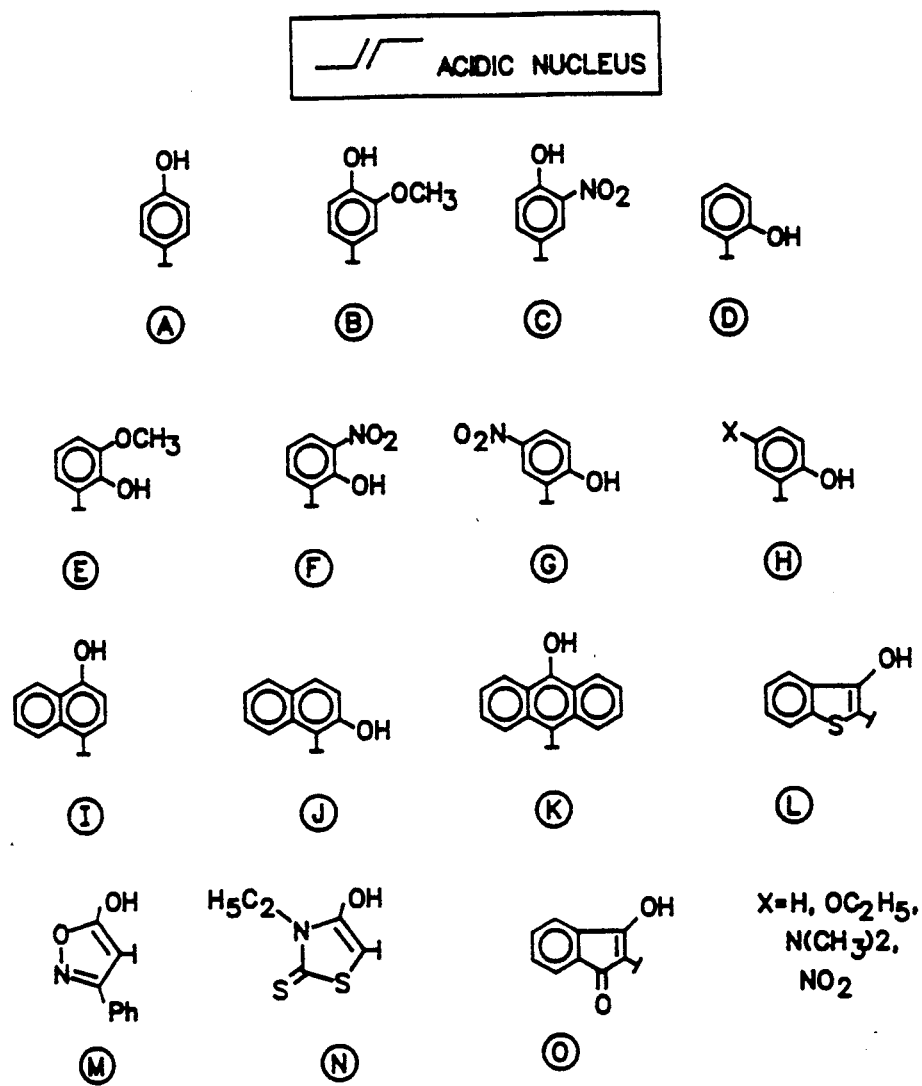
Figure 2:
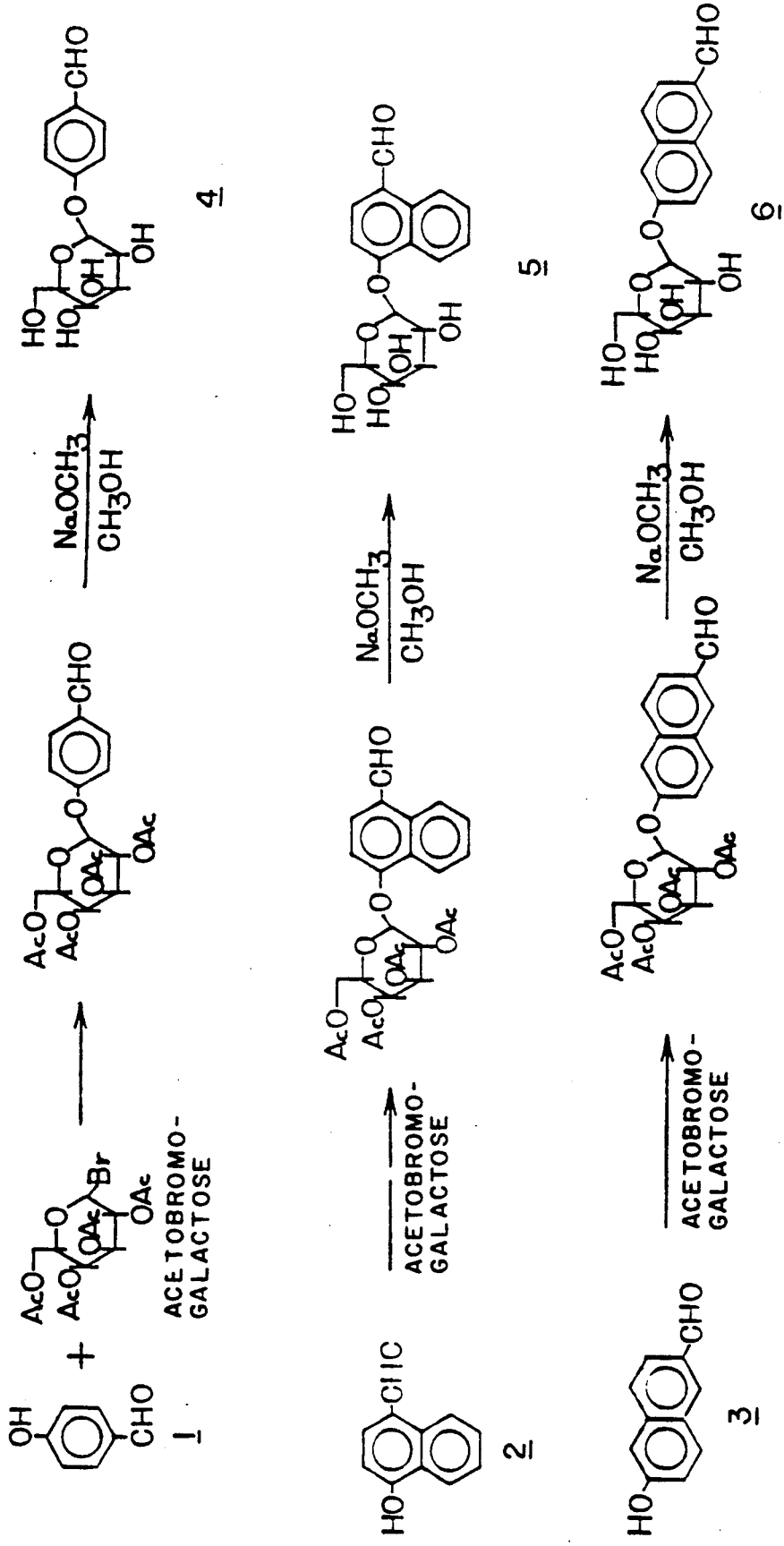
FIGS. 2 through 5 are flow diagrams of the principal steps in the preferred convergent synthesis of substrate compounds as described in the Examples.
Figure 3:
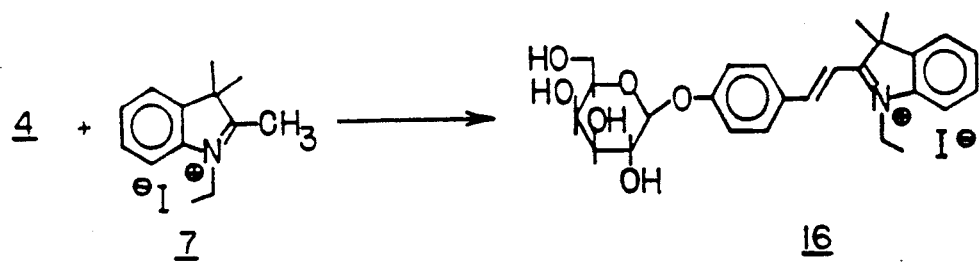
Figure 3:
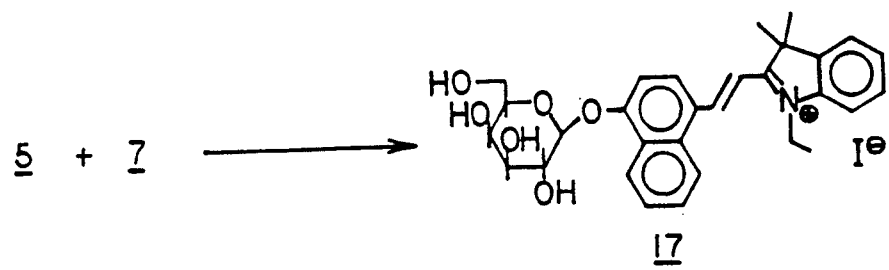
Figure 3:
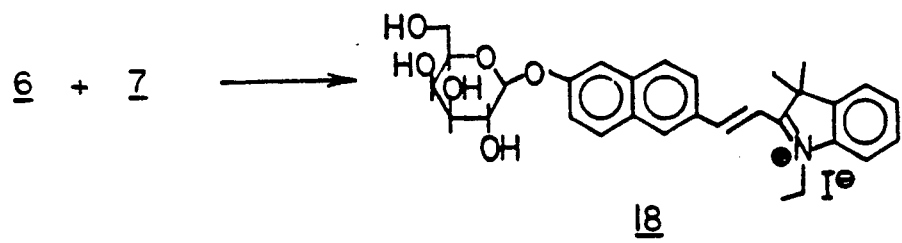
Figure 3:
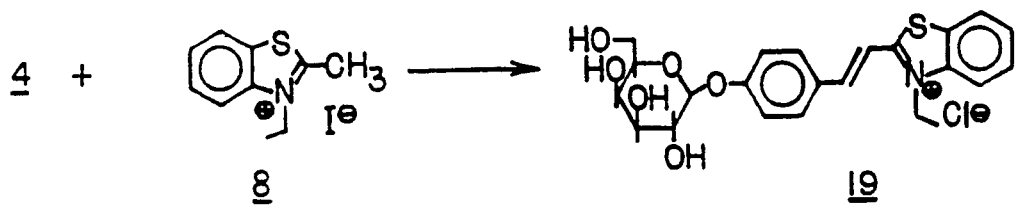
Figure 3:
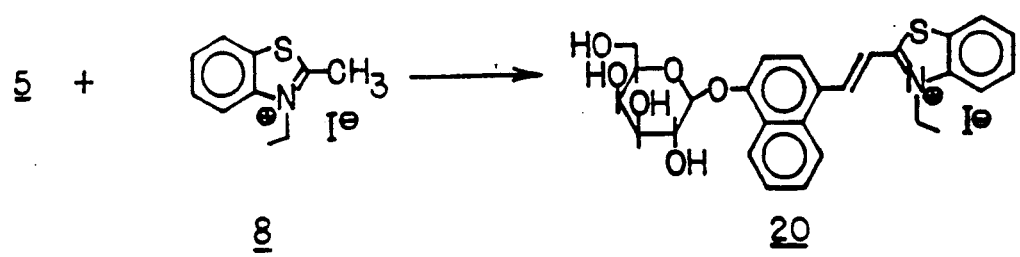
Figure 4:
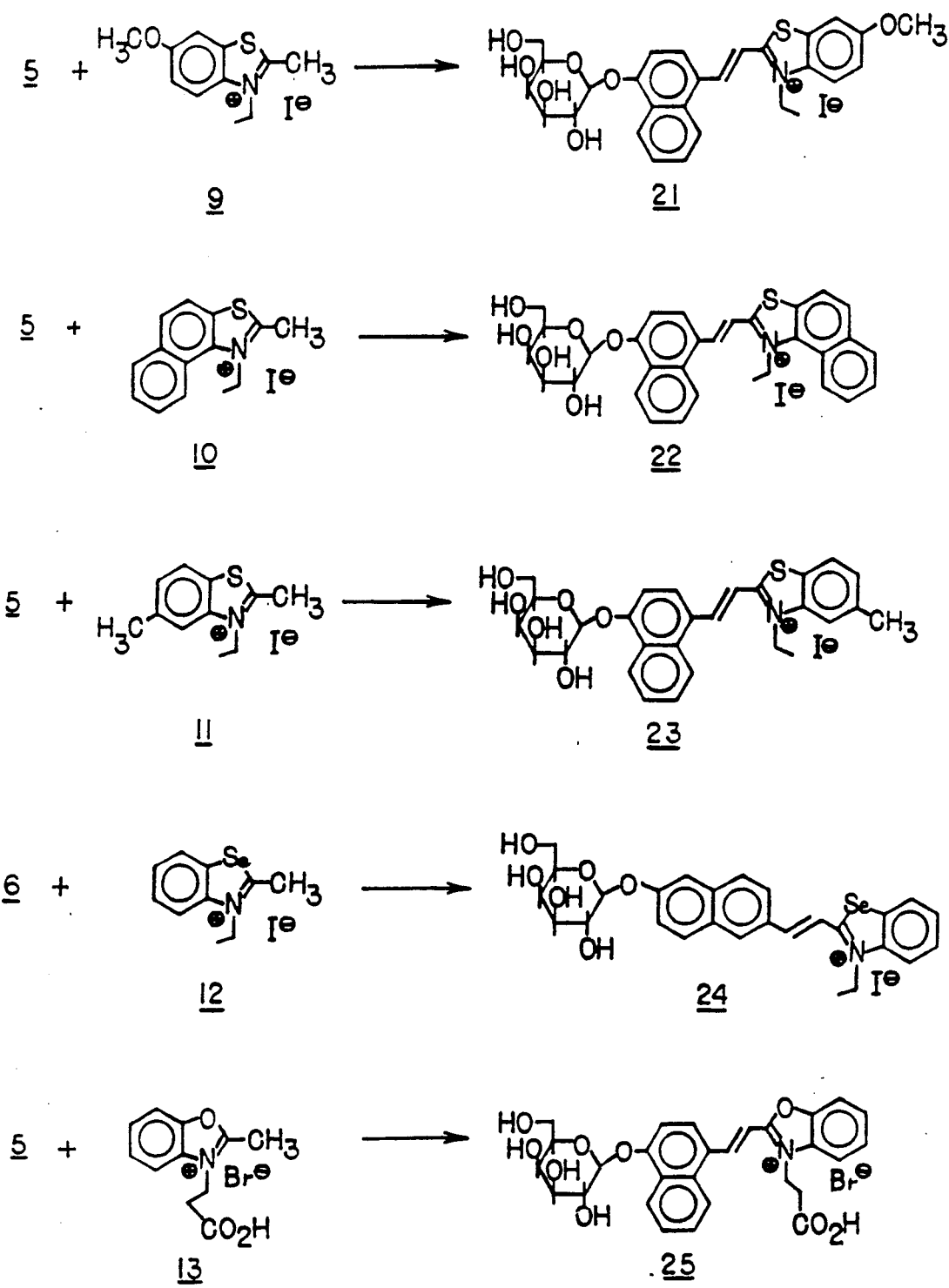
Figure 5:
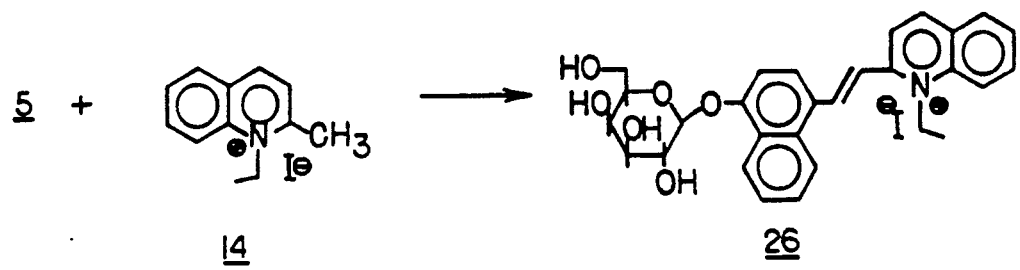
Figure 5:
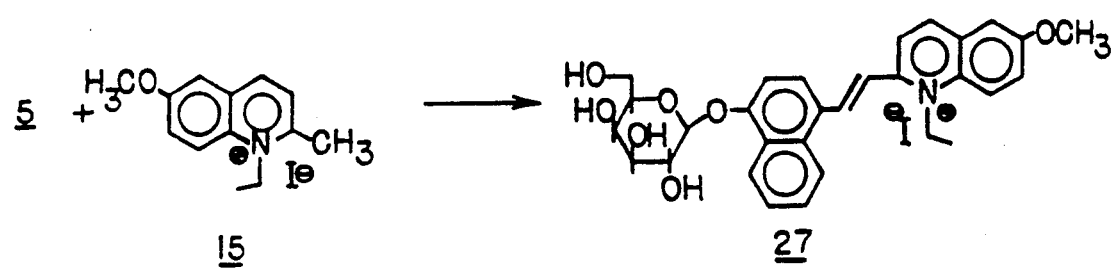
Figure 5:
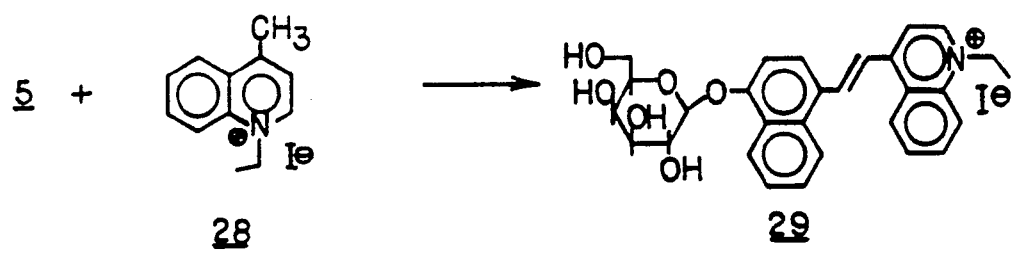

The merocyanines are a class of sensitizing dyes discovered independently in the early 1930's by Kendall (British Pat. Nos. 426,718; 428,222; 428,359; 428,360; 432,628; 549,201-4; 555,549; 555,550; 624,027; 624,951; and 634,952) and Brooker (U.S. Pat. Nos. 2,078,233; 2,089,729; 2,153,169; 2,161,331; 2,165,219; 2,165,338; 2,170,803-7; 2,177,401-3; 2,185,182; 2,185,343; 2,186,624; 2,211,762; and 2,332,433). The literature on these compounds has been the subject of several reviews—Quarterly Reviews 4,327(1950); "The Chemistry of Synthetic Dyes", vol. II, by K. Venkataraman, Academic Press, New York (1952), Chapter 38; "The Cyanine Dyes and Related Compounds" by F. Hamer, Interscience Publishers, New York (1964), chapters 10, 11 and 14; "The Chemistry of Synthetic Dyes, vol. IV, ed. K. Venkataraman, Academic Press, New York (1971), Chapter 5; and "The Chemistry of Heterocyclic Compounds", vol. 30, ed. E. Taylor and A. Weissberger, Wiley-Interscience, New York (1977).

Merocyanines are composed of an acidic nucleus and a basic nucleus as represented by the general formula (B)

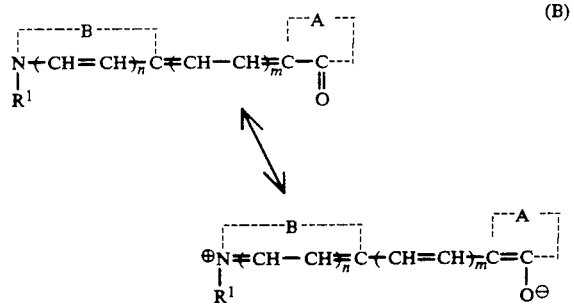

The chromophore in this molecule is the dipolar amidic system represented in formula (C).

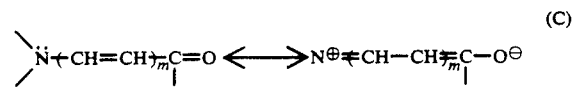

A simple merocyanine is defined as one in which the nuclei are directly linked, i.e., m=0 in formula (B) and a dimethinmerocyanine as one in which m=1 ("The Cyanine Dyes and Related Compounds", supra). Dimethinmerocyanines have also been called merocarbocyanines ("Kirk-Othmer Encyclopedia of Chemical Technology", vol. 7, 3rd ed., Wiley-Interscience, New York (1979), pp. 335-358). Homologs in which m=2 and 3 are also known. Synthetic methods for the preparation of this class of compounds have been recently reviewed ("The Chemistry of Heterocyclic Compounds", supra).

Among the merocyanine dyes, those of the stilbazolium betaine type [formula (D)] have found continuing interest because of their solvatochromatic properties.

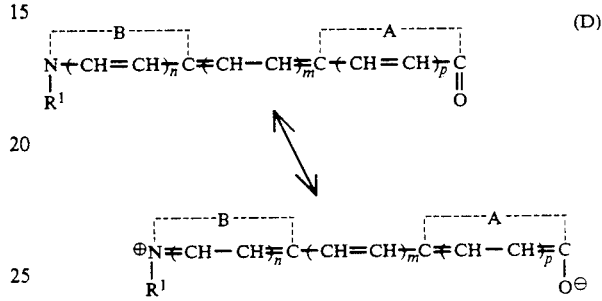

As early as 1920, a compound of this type was reported to function as a pH indicator, being "lemon-yellow" in the presence of acids and being "blood red" in the presence of alkali [L. F. Werner, J. Am. Chem. Soc. 42,2309(1920)]. Over the years, other pH indicators were recognized within this class of dyes [Helv. 23,247(1940); Ukran. Khim. Zhur. 18,347(1952); Farmacia (Bucharest) 22,345(1974)]. When the oxygen functionality of the acidic nucleus is derivatized, a shift in color from the underivatized dye has been noted [J. Org. Chem. 14,302(1949); Roczniki Chemii 37,225(1963)].

It is an object of this invention to prepare merocyanine dyes in which the oxygen functionality of the acidic nucleus has been derivatized with an enzyme cleavable group and to determine whether such compounds have utility as chromogenic enzyme substrates. As a result, it has been found that compounds of formula (A) are advantageous chromogenic enzyme substrates.

As used herein "alkyl" is intended to include linear and branched forms of unsubstituted hydrocarbon residues of the general formula—$C_nH_{2n+1}$, preferably of the "lower alkyl" aliphatic type wherein n is 6 or less, such as methyl, ethyl, n-propyl, iso-propyl, n-butyl, iso-butyl, tert-butyl, n-hexyl, and the like, as well as substituted forms thereof.

Further, "aryl" is intended to include organic residues derived from an aromatic hydrocarbon ring or ring system by removal of a hydrogen atom, and include the unsubstituted hydrocarbon ring residues such as phenyl and naphthol, and substituted forms thereof. For purposes of the present invention, aryl residues include those bearing one or more same or different functional groups or substituents which can be selected by one skilled in the art to provide the chromogenic enzyme substrate compounds of the present invention.

More particularly, where "aryl" and "alkyl" are substituted, such substitution is intended to include such groups or substituents when mono- or polysubstituted with functional groups which do not substantially negate the useful features of the present compounds. Such functional groups include chemical groups which may be introduced synthetically and result in the stable and useful chromogenic enzyme substrate indicator compounds of the present invention. Examples of such functional groups include, but are not intended to be limited to, halo (e.g., fluoro, chloro, bromo), substituted amino such as dialkylamino, nitro, alkoxy, aryloxy, alkyl, aryl, cyano, sulfo, carboxy, and alkoxycarbonyl.

ENZYMATICALLY-CLEAVABLE GROUPS

According to the present invention, the enzymatically-cleavable group Y is a radical of a compound Y-OH comprising an enzyme-specific moiety to provide novel chromogenic enzyme substrate compounds which confer specificity to a wide variety of enzymes encountered in a clinical chemistry, particularly hydrolases. The compound Y-OH is intended to include, but is not necessarily limited to, sugars and derivatives thereof, acyl groups including aliphatic and aromatic carboxylic acids, amino acids and peptides, and inorganic acids such as phosphoric and sulfuric acid groups.

It is to be understood that it will be evident to one skilled in the art that the selection of the enzymatically-cleavable group Y will depend, of course, upon the particular enzyme of interest. For example, where the enzyme of interest is a glycosidase, a glycoside can be prepared in which the enzymatically-cleavable group Y is the glycosidic radical corresponding to the natural substrate for the particular glycosidase. Suitable glycosidic radicals include, but are not intended to be limited to, mono- and oligosaccharide radicals, which are capable of being incorporated into a glycoside substrate specific for a particular glycosidase enzyme and cleaved by said enzyme, such as radicals of β-D-galactopyranose, α-D-galactopyranose, β-D-glucopyranose, α-D-glucopyranose and α-D-mannopyranose, as well as amino sugars such as N-acetylglucosamine and N-acetylneuraminic acid, and the like radicals. Other suitable glycosidic radicals include oligosaccharide chains from between about 2 to 20, preferably 2 to 7, monosaccharide units attached by α-1→4 glucosidic linkages, which can be broken down by saccharide-chain splitting enzymes to a mono- or oligosaccharide which, in turn, can be cleaved by a corresponding glycosidase, such as, for example, radicals of maltopentose, maltohexose and maltoheptose.

It is to be understood that in some instances where the glycosidic radical is an oligosaccharide chain as heretofore described, such chain is first modified or broken down to a shorter oligosaccharide or monosaccharide by the enzyme under determination to produce a secondary substrate compound in which the enzymatically-cleavable group is cleaved from the merocyanine indicator group by a secondary enzyme, in which case the secondary compound is then contacted with the secondary enzyme to generate a measurable change in absorbance as heretofore described. For example, where the enzyme under determination is α-amylase, the oligosaccharide chain is cleaved to produce a secondary glycoside substrate compound, e.g., an α-glucoside or β-glucoside, in which the resulting glycoside group thereof is cleavable from the merocyanine indicator group by a secondary glycosidase enzyme, e.g., α-glucosidase or β-glucosidase, respectively.

In the case of nonspecific esterase enzymes, the enzymatically-cleavable group Y is an acyl radical group of the formula

Where V is lower alkyl or aryl, such compounds can be employed for the detection of nonspecific esterase enzymes such as cholinesterase, acylase, lipase, and the like.

The chromogenic enzyme substrate compounds of the present invention can also be utilized for the detection of proteolytic enzymes commonly found in leukocytes. Such compounds are esters of the general formula where Y is a radical of the compound Y-OH and where Y-OH is an N-protected amino acid or short peptide, e.g., consisting of between about 2 to 5 amino acid units. For example, Y can be an N-protected amino acid N-tosyl-L-alanine radical. It will be appreciated that the present invention contemplates other carboxylic acid residues, amino acid residues and N-protecting groups as equivalents, as will be described in greater detail hereafter.

Similarly, for the detection of alkaline phosphatase from a liquid test sample, the enzymatically-cleavable group Y is a radical of the compound Y-OH wherein Y-OH is a phosphoric acid group.

BASIC AND ACIDIC NUCLEI

An extremely wide variety of different substituted and unsubstituted basic and acidic nuclei can be used to form the merocyanine dye component of the present compounds. Merocyanines reported in the literature are exemplified by those combinations of the basic and acidic nuclei depicted in FIG. 1 that are listed in Table A. These can be used in forming the present compounds where —OY will be substituted for —OH on the acidic nucleus. Other examples of merocyanine dyes are found in the various reviews, patents, and other literature cited herein.

BASIC NUCLEI

One skilled in the art of dye synthesis will recognize that virtually any basic nucleus known can be incorporated into the present compounds. The basic nucleus will fundamentally be a 5- or 6-membered N-containing heterocyclic ring or a fused ring system consisting of 5- and/or 6-membered heterocyclic or carbocyclic rings. Accordingly, in formula (A), B represents an appropriate residue to complete such basic nuclei. Representative of suitable nonmetallic atomic groups are C, S, O, N, and Se. The 5- or 6-membered heterocyclic rings are rings consisting of carbon atoms and one or more heteroatoms selected from N, O, S or Se joined by single and/or double bonds, and are represented by the nuclei shown in Table B.

TABLE A

| Merocyanine Dye (Basic Nucleus-Acid Nucleus) | Literature Reference |
| --- | --- |
| 1-A | J. Chem. Soc., 3313 (1955); J. Org. Chem. 14, 302 (1949); J. Am. Chem. Soc. 73, 5350 (1951); J. Gen. Chem. USSR 17, 1468 (1947); Farmacia (Bucharest) 22, 345 (1974); J. Chem. Ed. 54, 709 (1977). |
| 1-D | Farmacia (Bucharest) 22, 345 (1974). |
| 1-I | Ann. 592, 161 (1955). |
| 1-K | Ann. 592, 161 (1955). |
| 1-M | J. Am. Chem. Soc. 73, 5350 (1951). |

TABLE A-continued

| Merocyanine Dye (Basic Nucleus-Acid Nucleus) | Literature Reference |
|---|---|
| 2-A | J. Chem. Soc., 3313 (1955). |
| 2-C | J. Chem. Soc., 3038 (1951). |
| 2-D | Farmacia (Bucharest) 22, 345 (1974). |
| 2-F | J. Chem. Soc., 3038 (1951). |
| 2-I | Ukran. Khim. Zhur. 18, 347 (1952). |
| 2-O | J. Am. Chem. Soc. 73, 5356 (1951). |
| 3-J | Helv. 23, 247 (1940). |
| 4-A | J. Chem. Soc., 3313 (1955); Chem. Ber. 74, 471 (1941); Ann. 592, 161 (1955); Farmacia (Bucharest) 22, 345 (1974). |
| 4-I | J. Gen. Chem. USSR 17, 1468 (1947). |
| 4-K | J. Gen. Chem. USSR 17, 1468 (1947). |
| 5-A | J. Am. Chem. Soc. 42, 2309 (1920); J. Gen. Chem. (USSR) 10, 600 (1940); Chem. Ber. 74, 471 (1941); Roczniki Chemii 37, 225 (1963). |
| 5-B | J. Am. Chem. Soc. 42, 2309 (1920). |
| 5-C | J. Chem. Soc., 3038 (1951). |
| 5-D | J. Am. Chem. Soc. 42, 2309 (1920); J. Gen. Chem. (USSR) 10, 600 (1940). |
| 5-F | J. Chem. Soc., 3038 (1951). |
| 5-G | Ukran. Khim. Zhur. 18, 347 (1952). |
| 5-I | Ukran. Khim. Zhur. 18, 347 (1952). |
| 5-J | Helv. 23, 247 (1940). |
| 5-L | J. Chem. Soc., 2135 (1952). |
| 5-N | J. Am. Chem. Soc. 73, 5332 (1951). |
| 6-D | Helv. 23, 247 (1940). |
| 6-E | Helv. 23, 247 (1940). |
| 6-I | Ann. 592, 161 (1955). |
| 6-J | Helv. 23, 247 (1940). |
| 7-A | J. Am. Chem. Soc. 73, 5330 (1951). |
| 7-C | J. Chem. Soc., 3038 (1952). |
| 7-D | Helv. 23, 247 (1940). |
| 7-E | Helv. 23, 247 (1940). |
| 7-I | Ukran. Khim. Zhur. 18, 347 (1952). |
| 7-J | Helv. 23, 247 (1940). |
| 7-L | J. Chem. Soc. 2135 (1952). |
| 8-A | J. Am. Chem. Soc. 73, 5350 (1951). |
| 8-N | J. Am. Chem. Soc. 73, 5332 (1951). |
| 9-D | Helv. 23, 247 (1940). |
| 9-E | Helv. 23, 247 (1940). |
| 9-J | Helv. 23, 247 (1940). |
| 10-J | J. Chem. Soc., 3038 (1951). |
| 11-A | J. Gen. Chem. (USSR) 10, 600 (1940); Farmacia (Bucharest) 22, 347 (1974). |
| 11-D | J. Gen. Chem. (USSR) 10, 600 (1940). |
| 11-I | Ukran. Khim. Zhur. 18, 347 (1952). |
| 12-A | J. Gen. Chem. (USSR) 10, 600 (1940); Farmacia (Bucharest) 22, 347 (1974). |
| 12-I | Ukran. Khim. Zhur. 18, 347 (1952). |
| 13-I | Ukran. Khim. Zhur. 18, 347 (1952). |
| 13-L | J. Chem. Soc. 2135 (1952). |
| 14-A | J. Am. Chem. Soc. 73, 5350 (1951). |
| 15-A | J. Gen. Chem. (USSR) 10, 600 (1940); J. Am. Chem. Soc. 73, 5350 (1951); Ukran. Khim. Zhur. 18, 347 (1952); Roczniki Chemii 37, 225 (1963); Farmacia (Bucharest) 22, 345 (1974). |
| 15-C | J. Chem. Soc., 3038 (1951). |
| 15-D | J. Gen. Chem. (USSR) 10, 600 (1940). |
| 15-I | Ukran. Khim. Zhur. 18 347 (1952). |
| 15-J | Helv. 23, 247 (1940). |
| 15-L | J. Chem. Soc. 2135 (1952). |
| 15-N | J. Am. Chem. Soc. 73, 5332 (1951). |
| 16-A | J. Am. Chem. Soc. 73, 5350 (1951). |
| 17-A | J. Am. Chem. Soc. 73, 5350 (1951). |
| 18-H | J. Gen. Chem. USSR 17, 1468 (1947). |
| 18-L | J. Gen. Chem. USSR 17, 1468 (1947). |
| 19-A | Ukran. Khim. Zhur. 18, 347 (1952). |
| 19-I | Ukran. Khim. Zhur. 18, 347 (1952). |
| 19-L | J. Chem. Soc., 2135 (1952). |
| 20-I | Ukran. Khim. Zhur. 18, 347 (1952). |
| 20-L | J. Chem. Soc., 2135 (1952). |
| 21-J | Helv. 23, 247 (1940). |
| 21-L | J. Chem. Soc., 2135 (1952). |

The nuclei shown in Table B are merely a few examples of useful rings and ring systems for the basic nuclei. It will be evident that others can also be used for this purpose as well as various derivative and substituted forms of the nuclei depicted.

A particularly preferred basic nucleus is of formula (E)

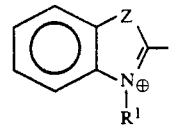

(E)

wherein Z is disubstituted methylene, e.g., di(lower alkyl)methylene, vinylene, alkyl- or aryl-substituted N, e.g., lower alkyl or phenyl substituted N, O, S, or Se, $R^1$ is as described herein, and wherein the phenyl group depicted in the formula is substituted or unsubstituted. The basic nucleus can be unsubstituted or bear substituents of such type and of such number on a given nucleus which will not interfer substantially with the ultimate chromogenic substrate properties desired. Such substituents will be recognized to include alkyl, particularly lower alkyl, aryl, particularly phenyl and substituted phenyl, alkoxy, aryloxy, halo, nitro and amino or substituted amino, e.g., dialkylamino, cyano, sulfo, carboxyl, carboxyalkyl, carboxamide, and carboxamidoalkyl.

TABLE B (1) 5-membered heterocyclic rings $Z = O, S, Se, N-R^1$
$W^1, W^2 = H, alkyl, aryl$
$R^1 = alkyl$ (2) 6-membered heterocyclic rings $W^3 = H, alkyl, aryl$
$R^1 = alkyl$ (3) fused heterocyclic-2 ring system $Z = NR^1, O, S, Se, CH_2, C(CH_3)_2$
$W^4 = H, alkyl, aryl, alkoxy, NR_2^1, NO_2, halo, cyano, aryloxy$
$R^1 = alkyl, aryl, carboxyalkyl, sulfoalkyl$

TABLE B-continued

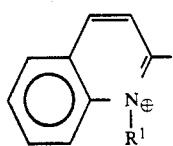

(4) fused heterocyclic-3 ring system

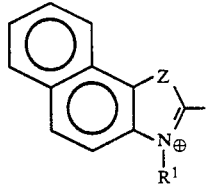

Z = S, O, Se, N—R¹
R¹ = alkyl, aryl, carboxyalkyl, sulfoalkyl

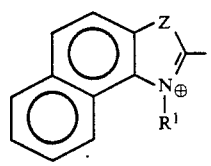

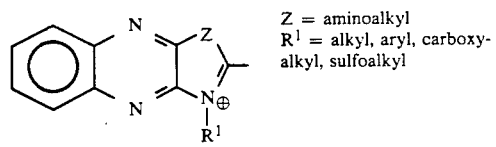

Z = aminoalkyl
R¹ = alkyl, aryl, carboxyalkyl, sulfoalkyl

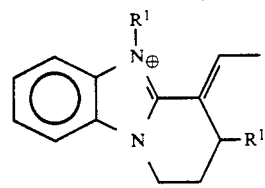

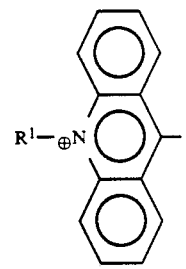

Representative examples of basic nuclei are thiazole, 4-methylthiazole, 4-phenylthiazole, 4,5-dimethylthiazole, 4,5-diphenylthiazole, benzothiazole, 4-chlorobenzothiazole, 5-chlorobenzothiazole, 6-chlorobenzothiazole, 7-chlorobenzothiazole, 5-nitrobenzothiazole, 6-nitrobenzothiazole, 4-methylbenzothiazole, 5-methylbenzothiazole, 6-methylbenzothiazole, 5-bromobenzothiazole, 6-bromobenzothiazole, 5-iodobenzothiazole, 5-phenylbenzothiazole, 5-methoxybenzothiazole, 6-methoxybenzothiazole, 5-ethoxybenzothiazole, 5-ethoxycarbonylbenzothiazole, 5-phenethylbenzothiazole, 5-fluorobenzothiazole, 5-chloro-6-nitrobenzothiazole, 5-trifluoromethylbenzothiazole, 5,6-dimethylbenzothiazole, tetrahydrobenzothiazole, 4-phenylbenzothiazole, 5-phenylbenzothiazole, naphtho(2,1-d)thiazole, naphtho(1,2-d)thiazole, naphtho(3,4-d)thiazole, 5-methoxynaphtho(1,2-d)thiazole, 7-ethoxynaphtho(2,1-d)thiazole, 8-methoxynaphtho(2,1-d)thiazole, 5-methoxynaphtho(3,4-d)thiazole, oxazole, 4-methyloxazole, 4-nitrooxazole, 5-methyloxazole, 4-phenyloxazole, 4,5-diphenyloxazole, 4-ethyloxazole, benzoxazole, 5-chlorobenzoxazole, 5-methylbenzoxazole, 5-bromobenzoxazole, 5-fluorobenzoxazole, 5-phenylbenzoxazole, 5-methoxybenzoxazole, 5-trifluoromethylbenzoxazole, 5-nitrobenzoxazole, 5-methylbenzoxazole, 6-chlorobenzoxazole, 6-nitrobenzoxazole, 6-methoxybenzoxazole, 6-hydroxybenzoxazole, 5,6-dimethylbenzoxazole, 4,6-dimethylbenzoxazole, 5-ethoxybenzoxazole, naphtho(2,1-d)oxazole, naphtho(1,2-d)oxazole, naphtho(3,4-d)oxazole, 5-nitronaphtho(3,2-d)oxazole, 4-methylselenazole, 4-nitroselenazole, 4-phenylselenazole, benzoselenazole, 5-chlorobenzoselenazole, 5-nitrobenzoselenazole, 5-methoxybenzoselenazole, 5-hydroxybenzoselenazole, 6-nitrobenzoselenazole, 5-chloro-6-nitrobenzoselenazole, naphtho(2,1-d)selenazole, naphtho(1,2-d)selenazole, 3,3-dialkylindolenine and ring substituted 3,3-dialkylindolenines, 1-alkylimidazole, 1-alkyl-4-phenylimidazole, 1-alkylbenzimidazole, 1-alkyl-5-methoxybenzimidazole, 1-alkyl-5-cyanobenzimidazole, 1-alkyl-5-fluorobenzimidazole, 1-alkyl-5-trifluoromethylbenzimidazole, 1-alkylnaphtho(1,2-d)imidazole, 1-aryl-5,6-dichlorobenzimidazole, 1-aryl-5-chlorobenzimidazole, 1-arylimidazole, 1-arylbenzimidazole, 1-aryl-5-chlorobenzimidazole, 1-aryl-5,6-dichlorobenzimidazole, 1-aryl-5-methoxybenzimidazole, 1-aryl-5-cyanobenzimidazole, 1-arylnaphtho(1,2-d)imidazole, wherein the alkyl group is methyl, ethyl, propyl, isopropyl, butyl, 2-hydroxyalkyl, 3-hydroxypropyl, and the like, and the aryl group is phenyl, a substituted phenyl, a methyl-substituted phenyl or a methoxy-substituted phenyl. Examples of the basic nucleus further include 2-pyridine, 4-pyridine, 5-methyl-2-pyridine, 3-methyl-4-pyridine, and quinoline nuclei, (e.g., 2-quinoline, 3-methyl-2-quinoline, 5-ethyl-2-quinoline, 6-methyl-2-quinoline, 6-methoxy-2-quinoline, 8-chloro-2-quinoline, 4-quinoline, 6-ethoxy-4-quinoline, 6-nitro-4-quinoline, 8-chloro-4-quinoline, 8-fluoro-4-quinoline, 8-methyl-4-quinoline, and 8-methoxy-4-quinoline).

Particularly preferred basic nuclei are the substituted and unsubstituted forms of indolenine, naphthothiazole, benzoxazole, benzothiazole, quinoline, thiazole, rhodanine, benzoselenazole, and benzimidazole, and particularly include 4-methylthiazole, 4-phenylthiazole, benzothiazole, 5-chlorobenzothiazole, 5-methylbenzothiazole, 6-methoxybenzothiazole, naphtho(2,1-d)thiazole, naphtho(1,2-d)thiazole, benzoxazole, 5-methylbenzoxazole, benzoselenazole, 3,3-dimethylindolenine, 4-quinoline, 2-quinoline, 6-methoxy-2-quinoline and 4-pyridine.

Substituent R¹ on the basic nucleic as depicted in formula (A) can generally be alkyl or aryl as defined above, and preferably is substituted or unsubstituted lower alkyl or phenyl. Examples, without limitation, are methyl, ethyl, propyl, butyl, benzyl, phenyl, β-phenyethyl, 1-hydroxyethyl, 2-methoxyethyl, 2-(2-methoxyethoxy)-ethyl, carboxymethyl, 2-carboxyethyl, 3-carboxypropyl, 4-carboxybutyl, 2-sulfoethyl, 3-sulfopropyl, 3-sulfobutyl, 4-sulfobutyl, 2-(pyrrolidin-2-on-1-yl)ethyl, tetrahydrofurfuryl, 2-acetoxyethyl, carbomethoxymethyl, and 2-methanesulfonylaminoethyl.

As depicted in formula (A), and implied when describing cationic basic nuclei as in FIG. 1, the merocyanine compounds have a corresponding counterion (anion) X. The nature of the counterion, whether the compound of formula (A) is in an ionized or nonionized form, is believed not to be critical to the present invention, although solubility may be affected by the nature of the counter ion (see The Chemistry of Synthetic Dyes, vol. 4, supra, p. 294). Accordingly, such counter ion can take a wide variety of forms. Just a few of the commonly found counter ions (which complex with the merocyanine from the reaction mixture in which they are synthesized or the solutions in which they are dissolved) are chloride, bromide, iodide, tetrafluoroborate, trifluoroacetate, acetate, sulfate, tosylate, phosphate, and perchlorate.

ACIDIC NUCLEI

As in the case of the basic nucleus, the acidic nucleus can vary widely as is known in the art (FIG. 1, Table A, and cited references, supra). The acidic nucleus will fundamentally be a 5- or 6-membered carbocyclic or heterocyclic ring or a fused ring system consisting of 5- and/or 6-membered carbocyclic or heterocyclic rings. Accordingly, in formula (A), A represents an appropriate residue to complete such acidic nuclei. Representative of suitable nonmetallic atomic groups are C, S, O, N and Se. As 5- or 6-membered carbocyclic rings are intended rings consisting of 5 or 6 carbon atoms joined by single and/or double bonds. As 5- or 6-membered heterocyclic rings are intended rings consisting of carbon atoms and one or more heteroatoms selected from N, O, S or Se joined by single and/or double bonds. Table C depicts some representative carbocyclic and heterocyclic rings and fused ring systems that can serve as the acidic nuclei. The depicted structures are merely a few examples of particular acidic nuclei. It will be evident that others can also be used for this purpose as well as various derivative and substituted forms of the nuclei depicted.

Particularly preferred acidic nuclei are substituted or unsubstituted 1,2-naphthylene, 1,4-phenylene, 1,4-naphthylene, and 2,6-naphthylene.

Representative examples of acidic nucleic are 3-alkylrhodanine, 3-arylrhodanine, 1-alkyl-2-pyrazolin-5-one, 3-aryl-5-oxazolone, 1,3-dialkyl-2-thiohydantoin (1,3-dialkyl-2-thio-2,4-imidazolidinedine), 1,3-diaryl-2-thiohydantoin (1,3-diaryl-2-thio-2,4-imidazolidinedione nucleus), 1,3-dialkyl-2-thiobarbituric acid, 3-alkyl-4-thiazolidinone, 3-aryl-4-thiazolidinone, indan-1,3-dione, thioindoxyl, 1,3-dialkylhydantoin (1,3-dialkyl-2,4-imidazolidinedione nucleus), 1,3-diarylhydantoin (1,3-diaryl-2,4-imidazolidinedione nucleus), 4-hydroxyphenyl, 4-hydroxy-3-methoxyphenyl, 4-hydroxy-3-nitrophenyl, 2-hydroxyphenyl, 2-hydroxy-3-methoxyphenyl, 2-hydroxy-3-nitrophenyl, 2-hydroxy-4-nitrophenyl, 2-hydroxy-5-ethoxyphenyl, 2-hydroxy-5-dimethylaminophenyl, 4-hydroxy-1-naphthyl, 2-hydroxy-1-naphthyl, 9-hydroxy-10-anthryl, 4-hydroxy-1-anthryl, 6-hydroxy-2-naphthyl and 5-hydroxy-1-naphthyl. Preferred acidic nuclei include 4-hydroxy-1-phenyl, 4-hydroxy-3-nitrophenyl, 2-hydroxyphenyl, 4-hydroxy-1-naphthyl, 2-hydroxy-1-naphthyl, 6-hydroxy-2-naphthyl, 5-hydroxy-1-naphthyl and 4-hydroxy-1-anthryl.

TABLE C (1) 4-membered rings

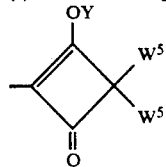

$W^5$ = alkyl (2) 5-membered rings

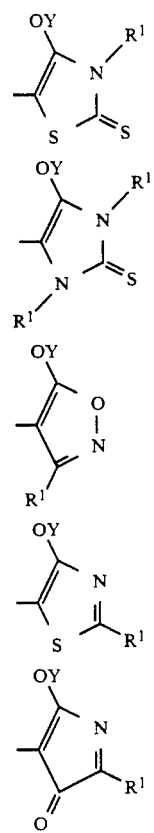

$R^1$ = alkyl, aryl, carboxyalkyl, sulfoalkyl (3) 6-membered rings

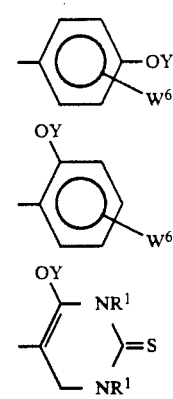

$W^6$ = alkyl, aryl, alkoxy, aryloxy, cyano, halo, nitro, carboxycarbonyl (4) fused ring-2 ring system

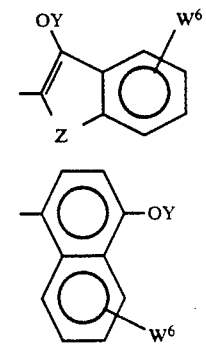

Z = S, carbonyl
$W^6$ = alkyl, aryl, alkoxy, aryloxy, cyano, halo, nitro, carboxycarbonyl

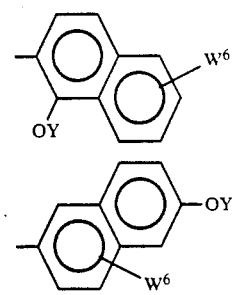

(5) fused ring-3 ring system

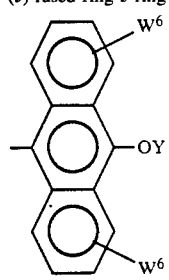

$W^6$ = alkyl, aryl, alkoxy, aryloxy, cyano, halo, nitro, carboxycarbonyl

The basic and acidic nuclei are joined, as depicted in formula (A) by a single bond (m=0) or conjugated vinylene groups (m=1-3). Dimethinmerocyanines, where m=1, are most common and preferred. Geometry about this double bond is usually trans, but the cis orientation is also contemplated. Where m=1, the bridge carbons can be substituted or unsubstituted, e.g., $R^2$ and $R^3$ can be the same or different and can be hydrogen, lower alkyl, or cyano.

A particularly preferred class of the merocyanine enzyme substrate compounds of the present invention are represented by the formula (F)

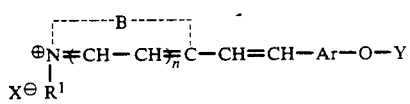

wherein Y is an enzymatically-cleavable group which is a radical of a compound Y-OH selected from sugars and derivatives thereof, aliphatic and aromatic carboxylic acids, amino acids, peptides, phosphoric acid, and sulfuric acid; B represents a non-metallic atomic group or residue which completes a 5- or 6-membered N-containing heterocyclic ring or a fused ring system consisting of three or less 5- and/or 6-membered heterocyclic or carbocyclic rings; $R^1$ is substituted or unsubstituted lower alkyl or aryl, e.g., phenyl; Ar is substituted or unsubstituted phenylene, naphthylene or anthrylene; n is an integer from 1 through 3; and X is a counterion (anion). Most commonly Y-OH will be α-D-galactose, β-D-galactose, α-glucose, β-glucose, α-mannose, N-acetylglucosamine, N-acetylneuraminic acid, or an oligosaccharide chain of from between about 2 to 20 monosaccharide units e.g., maltopentose, maltohexose, and maltoheptose. In the compounds of formula (F), Ar is preferably substituted or, more usually, unsubstituted 1,2-naphthylene, 1,4-phenylene, 1,4-naphthylene, or 2,6-naphthylene, and B completes a residue of substituted or unsubstituted indolenium, β-naphthothiazolium, benzoxazolium, benzothiazolium, quinolium, thiazolium, or rhodaninium, and more preferably is of formula (E).

Compounds that are particularly useful are of formula (G)

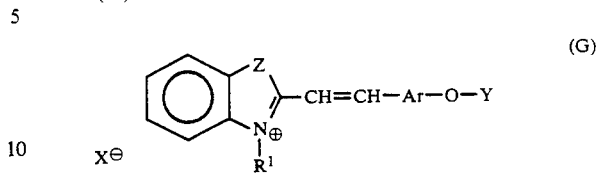

wherein Y is a radical of a compound Y-OH selected from sugars and derivatives thereof, particularly β-D-galactose; Ar is 1,4-phenylene, 1,4-naphthylene or 2,6-naphthylene; $R^1$ is substituted or unsubstituted lower alkyl, particularly ethyl or methyl; Z is di(lower alkyl)-methylene, vinylene, O, S, or Se, and wherein the phenyl ring is substituted or unsubstituted and X is a counterion (anion).

SYNTHESIS

Dye synthesis in general has been characterized in the literature as being of the condensation type, that is two intermediates reacting under suitable conditions with elimination of some simple molecule. This general description of the combining of nucleophilic and electrophilic reagents covers most methods of non-oxidative dye synthesis. Typically, the nucleophile is a methylene base derived from an active methyl quaternary salt, and the electrophile is an orthoester or aldehyde. Coupling of an active methyl quaternary salt (basic nucleus) with an aromatic aldehyde (acidic nucleus) under basic conditions is a common method used in the preparation of merocyanine dyes. Other methods are known as well and described in the literature cited herein.

In principle, one can first prepare a merocyanine dye with an available hydroxyl group on the acidic nucleus for subsequent modification to form the enzymatically cleavable group. In practice, however, this has been found to be generally unsuccessful, the condensed merocyanine dye being substantially unreactive to form the enzymatically cleavable group. This is likely due to the merocyanine being in the uncharged or neutral tautomeric form [see formula (B)] under the basic conditions required for condensation of the enzymatically cleavable group precursor.

Accordingly, a convergent synthesis has been devised in which the basic nucleus is condensed with an acidic nucleus that has already been modified to comprise the enzymatically cleavable group. As the first step in the synthesis, a class of aryl aldehyde intermediates are formed by reaction of a hydroxyl-functionalized arylaldehyde under appropriate conditions to incorporate the appropriate enzynmatically cleavable group. The resulting compounds will be of formula (H)

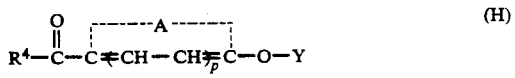

wherein A, Y and p are described herein above and $R^4$ is hydrogen or lower alkyl. Particularly novel are the intermediates of formula (J)

wherein Ar is substituted or unsubstituted phenylene, naphthylene, particularly 1,4-phenylene, 1,4-naphthylene or 2,6-naphthylene.

To prepare the present substrate compounds, such arylaldehydes are reacted with a quaternary salt derivative of formula (K)

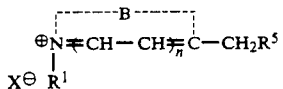 (K)

wherein B, $R^1$, n and X are as described above and $R^5$ is hydrogen, lower alkyl, or cyano, under appropriate basic conditions as are known in the art. Generally, arylaldehydes of the formula (J) are first dissolved or suspended in a suitable basic solvent, basic solvent mixture or solvent containing a base, which is capable of at least partially dissolving the arylaldehyde. Such basic solvents include pyridine, quinoline, piperidine, pyrrolidine, hexamethylphosporamide and di- and trialkylamines. Mixtures of these basic solvents with other solvents, including alcohols such as methanol and ethanol, ethers such as tetrahydroguran and dioxane, amides such as dimethylformamide and dimethylacetamide, aromatics such as toluene and benzene, haloalkanes such as chloroform and dichloromethane, ketones such as acetone and methylethylketone, and esters such as ethyl acetate, are also useful. Additionally, certain alkoxide bases such as sodium methoxide, sodium ethoxide and potassium tert-butoxide will be useful in alcoholic solvents such as methanol, ethanol and tert-butanol. A preferred solvent is pyridine. The solution or suspension of the arylaldehyde of the formula (J) is then treated, either at once or in portions over a period of from 10 minutes to 5 hours, preferably 0.25 to 2.25 hours, with 0.5 to 5.0 molar equivalents, preferably 1.0 to 1.5 molar equivalents, of quaternary salt of the formula (K). The reaction mixture is maintained at a temperature of 0° C. to 150° C., preferably 50° C. to 100° C., for a period of time from 1 minute to 36 hours, preferably 5 to 20 hours, then the solvent is removed under reduced pressure and the compound of the formula (E) is purified using methods known in the art, such as chromatography.

Preparation of the enzymatically cleavable group-modified arylaldehydes will proceed as appropriate for the cleavable group involved.

Glycosides of the reactive acidic nucleus can be prepared according to methods known in the art of carbohydrate chemistry employing known derivatives of carbohydrates of the formula Y-OH which are reacted with an appropriate acidic nucleus. Such carbohydrate derivatives, which in some instances carry protecting groups, are commercially available (Aldrich Chemical Co., Milwaukee, Wis., U.S.A.; Sigma Chemical Co., St. Louis, Mo., U.S.A.), or can be prepared according to methods known in the art (Methods in Carbohydrate Chemistry [Academic Press, 1963], Vol. 2). Glycosidic radicals which are suitable for coupling to the acidic nucleus to provide suitable glycosides of formula (H) include, but are not intended to be limited to, radicals of sugars such as β-D-galactopyranose, α-D-galactopyranose, β-D-glucopyranose, α-D-glucopyranose, α-D-mannopyranose, N-acetylglucosamine, β-glucuronic acid and neuraminic acid. Other suitable glycosidic radicals include radicals of oligosaccharide chains which by saccharide-chain splitting enzymes can be broken down to the level of a mono- or oligosaccharide, which in its turn can be directly split off from the dye nucleus with the corresponding glycosidase. It is to be understood that such oligosaccharide chains are chains consisting of 2 to 20, preferably 2 to 7 monosaccharide units, such as maltopentose, maltohexose or maltoheptose. The acidic nucleus is reacted with a mono- or oligosaccharide or a 1-halo-derivative thereof, where all hydroxyl groups are substituted with a protecting group according to methods known in the art of carbohydrate chemistry, to give per-O-substituted glycosides, from which the glycosides of the acidic nucleus are obtained by cleaving the protective groups according to methods known in the art.

The compounds of the general formula (H) where Y=H are reacted with the per-O-substituted 1-halosaccharides, preferably in the presence of proton acceptors such as alkali hydroxides or alkali carbonates, in aqueous acetone or (under phase transfer conditions) in a water/chloroform or water/benzene mixture. This procedure can furthermore be carried out by first converting the acidic nucleus with alkali hydroxide or alcoholate into alkali salts or, using possibly substituted amines, into ammonium salts, and then reacting these with the per-O-substituted 1-halosaccharides in dipolar aprotic solvents such as acetone, dimethylsulfoxide, dichloromethane, tetrahydrofuran or dimethylformamide. Furthermore in the synthesis of per-O-substituted glycosides from acidic nuclei and per-O-substituted 1-halosaccharides, additives in the form of single silver salts or mixtures of silver salts, such as silver oxide, silver carbonate, silver carbonate on Celite (Johns-Manville Corp., Denver, Colo., U.S.A.), silver triflate or silver salicylate, and/or of single mercury salts or mixtures of mercury salts, such as mercury bromide, mercury cyanide, mercury acetate or mercury oxide, and/or of single cadmium salts or mixtures of cadmium salts such as cadmium carbonate or cadmium oxide, possibly with the use of drying agents such as calcium chloride, a molecular seive or Drierite (W. A. Hammond Drierite Co., Xenia, Ohio, U.S.A.), in solvents such as methylene chloride, chloroform, benzene, toluene, ethyl acetate, quinoline, tetrahydrofuran or dioxane have proven effective. In the synthesis of α-linked glycosides, an acidic nucleus of the general formula (H) where Y=H is melted with a saccharide whose hydroxy groups are substituted with a protective group, preferably an acetyl-group, in the presence of a Lewis acid, such as zinc chloride (see Chem. Ber. 66, 378-383 [1933] and Methods in Carbohydrate Chemistry, Academic Press, 1967, Vol. 2, pp. 345-347). The temperature of the reaction is preferably between 80° and 130° C., more preferably between 110° and 130° C.

Removing the protecting groups from the per-O-substituted glycosides to form glycosides of general formula (H) is performed according to methods known in the art of carbohydrate chemistry (see Advances in Carbohydrate Chem. 12, 157 (1976), such as with the protective acyl-groups with sodium methylate, barium methylate or ammonia in methanol. Especially suitable as a protecting group commonly used in carbohydrate chemistry is an acetyl, benzoyl, benzyl or trimethylsilyl-radical.

Acidic nuclei of the general formula (H) where Y is the radical of an oligosaccharide chain of from about 2 to 20 monosaccharide units attached via α-1-4 glucosidic linkages can additionally be prepared from the α- and β- glucosides by an enzymatic process first described by French, et al., J. Am. Chem. Soc. 76, 2387 (1954), and later by Wallenfels, et al., Carbohydrate Research 61, 359 (1978), involving the transfer of the glucoside to a preformed polysaccharide chain by the enzyme (1-4)-α-glucan-4-glucosyltransferase (also known as cyclomaltodextrin glucanotransferase; EC 2.4.1.19).

Esters of merocyanine dyes of the general formula (A) are useful as chromogenic esterase and protease substrates. Such esters can be prepared by methods known in the art of organic chemistry by first reacting known derivatives of carboxylic acids with a suitable acidic nucleus to provide a reactive electrophilic acid nucleus derivative of the formula (H) where Y is

where V is alkyl, substituted alkyl (particularly aminoalkyl) or aryl. This derivative is then condensed with an active methyl quaternary salt of the formula (K) (basic nucleus) to afford chromogenic merocyanine enzyme substrates.

Such known derivatives of carboxylic acids of the formula Y-OH include, but are not intended to be limited to, amino acid residues, preferably residues of naturally occurring α-amino acids in their L- or D- form or also in their racemic form, the residues of glycine, alanine, valine, leucine, isoleucine, phenylalanine and tyrosine being preferred, the L- forms thereof being more preferred. Any free hydroxyl groups possibly present may be acylated and preferably acetylated. The peptide residues in this definition of Y-OH are to be understood to be, for example, amino acids or peptides from between about 2 to 5 amino acid units such as di-, tri-, tetra-, and pentapeptides, di- and tripeptides being preferred, the amino acid components thereof being the above-mentioned amino acids. It is also to be understood that the amino groups of such amino acids or peptides may be protected with nitrogen protecting groups known in the art of peptide chemistry (see T. W. Green, Protective Groups in Organic synthesis, J. Wiley and Sons, New York, N.Y., 1981, pp. 218-287) including, for example, acyl, oxycarbonyl, thiocarbonyl, sulphonyl, especially p-toluenesulphonyl (Tosyl, Ts), sulphenyl, vinyl, cyclohexenyl, and carbamoyl, especially t-butyl-(BOC) and benzyl-(CBz) carbamoyl radicals. Such esters may also be similarly prepared by reacting a compound of the general formula (H) where Y=H with a carboxylic acid, amino acid or peptide, Y-OH as defined above, or with an appropriate reactive derivative thereof, employing methods known in the art of organic chemistry (see J. March, Advanced Organic Chemistry: Reactions, Mechanism and Structure, McGraw-Hill Book Co., New York, NH, 1968, pp. 319-323). The reactive derivatives used can be, for example, acid chlorides or bromides, or mixed anhydrides conventionally used in peptide synthesis, such as those with ethyl chloroformate, or active esters such as those of N-hydroxysuccinimide.

Similarly, inorganic esters can be prepared according to methods known in the art of organic systhesis. The known derivatives of inorganic acids Y-OH, such as phosphoric acid, e.g., compound where

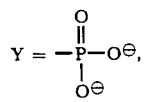

or sulfuric acid where

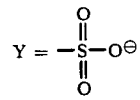

are reacted with a compound of the general formula (H) where Y=H employing methods known in the art of organic chemistry, such as shown in Koller and Wolfbeis, Monatsh. 116, 65 (1985) for inorganic esters of certain coumarins.

ANALYTICAL METHODS

The chromogenic enzyme substrate compounds of the present invention are useful in analytical test systems which require the measurement of the amount of enzyme present therein, particularly those analytical test systems employing enzyme-labeled assay reagents. Such analytical test systems include, but are not intended to be limited to, enzyme immunoassays known in the art as competitive, sandwich and immunometric techniques where the amount of enzyme label in a particular fraction thereof can be measured and correlated to the amount of analyte under determination obtained from a liquid test sample.

The use of specific binding substances, such as antigens, haptens, antibodies, lectins, receptors, avidin, and other binding proteins, and polynucleotides, labeled with an enzyme have been recently developed and applied to the measurement of substances in biological fluids (see, for example, Clin. Chem., Vol. 22, p. 1232 (1976); Reissue U.S. Pat. No. 31,006; and U.K. Patent No. 2,019,308). Generally, such measurement depends upon the ability of a binding substance, e.g., an antibody or an antigen, to bind to a specific analyte wherein a labeled reagent comprising such binding substance labeled with an enzyme is employed to determine the extent of such binding. Typically, the extent of binding is determined by measuring the amount of enzyme labels present in the labeled reagent which either has or has not participated in a binding reaction with the analyte, wherein the amount of enzyme detected and measured can be correlated to the amount of analyte present in a liquid test sample.

The chromogenic enzyme substrate compounds of the present invention are particularly useful in analytical test systems as heretofore described where an analytical test device comprising a carrier matrix incorporated with the chromogenic enzyme substrate compound of the present invention is employed, the nature of the enzyme-specific moiety thereof depending, of course, upon the particular enzyme being detected.

The nature of the material of such carrier matrix can be of any substance capable of being incorporated with the chromogenic enzyme substrate compound of the present invention, such as those utilized for reagent strips for solution analysis. For example, U.S. Pat. No. 3,846,247 describes the use of felt, porous ceramic strips, and woven or matted glass fibers. As substitutes for paper, U.S. Pat. No. 3,552,928 describes the use of wood sticks, cloth, sponge material, and argilaceous substances. The use of synthetic resin fleeces and glass fiber felts in place of paper is suggested in British Pat. No. 1,39,139, and British Pat. No. 1,349,623 teaches the use of a light-permeable meshwork of thin filaments as a cover for an underlying paper matrix. This reference also teaches impregnating the paper with part of a reagent system and impregnating the meshwork with other potentially incompatible reagents. French Pat. No. 2,170,397 describes the use of carrier matrices having greater than 50% polyamide fibers therein. Another approach to carrier matrices is described in U.S. Pat. No. 4,046,513 wherein the concept of printing reagents onto a suitable carrier matrix is employed. U.S. Pat. No. 4,046,514 describes the interweaving or knitting of filaments bearing reagents in a reactant system. All such carrier matrix concepts can be employed in the present invention, as can others. Preferably, the carrier matrix comprises a bibulous material, such as filter paper, whereby a solution of the chromogenic enzyme substrate compound of the present invention is employed to impregnate the matrix. It can also comprise a system which physically entraps the assay reagents, such as polymeric microcapsules, which then rupture upon contact with the test sample. It can comprise a system wherein the assay reagents are homogeneously combined with the carrier matrix in a fluid or semi-fluid state, which later hardens or sets, thereby entrapping the assay reagents.

In a preferred embodiment, the carrier matrix is a bibulous material in the form of a zone or layer incorporated with the chromogenic enzyme substrate compound of the present invention which is employed where a particular assay is performed in a liquid environment employing an insoluble assay reagent known in the art to physically separate the free species of the labeled reagent from the bound species of the labeled reagent. According to such assay system, an aliquot of liquid containing the free species is removed and applied to the carrier matrix wherein the chromogenic enzyme substrate compound incorporated therein interacts with the enzyme label of the labeled reagent of the free species from the liquid test sample to provide a detectable signal which can be visibly observed and/or measured with an appropriate instrument, such as a spectrophotometer.

Similarly, a test device comprising two or more carrier matrices in the form of, for example, an uppermost layer or zone and a lowermost layer or zone can be employed. The lowermost layer of such test device can be incorporated with the chromogenic enzyme substrate compound of the present invention wherein a liquid test sample containing analyte under determination is applied to the uppermost layer of the device. The analyte which diffuses therein participates in the necessary binding reactions to generate a free and bound (i.e., immobilized) species of the enzyme labeled reagent therein as described above. Accordingly, the free species of the labeled reagent so generated is free to migrate into the lowermost layer where the enzyme label of the free species cleaves the enzymatically-cleavable group of the chromogenic enzyme substrate compound of the present invention incorporated therein to provide a measurable, detectable signal as heretofore described.

The present invention will now be illustrated, but is not intended to be limited, by the following examples.

EXAMPLES

The synthesis of merocyanine substrates as described in the Examples below involves two major steps. With reference to FIGS. 2 through 5 of the drawings, the first step is the synthesis of a $\beta$-D-galactopyranosyloxyarylaldehyde from tetra-acetyl-protected bromo-$\alpha$-D-galactose and the corresponding hydroxyarylaldehyde in the presence of silver (I) oxide and quinoline followed by deprotection of the hydroxyl group by alkaline hydrolysis with sodium methoxide. The second step is the coupling of the substrate-modified arylaldehyde with an active methyl quaternary amine salt to give the corresponding merocyanine substrate.

A. Preparation of Arylaldehyde Intermediates 4-($\beta$-D-Galactopyranosyloxy)-benzaldehyde (4)—A solution of 4-hydroxybenzaldehyde (1) (Aldrich Chemical Co., Inc., Milwaukee, Wis., U.S.A.) (6.1 g; 50 mmol) in 1M NaOH (50 mL) was treated at ambient temperature with a solution of acetobromo-$\alpha$-D-galactose (Sigma Chemical Co., St. Louis, Mo., U.S.A.) (10.28 g; 25 mmol) in acetone (200 mL). The reaction mixture was stirred for 22 hours, then the acetone was removed under reduced pressure and the aqueous residue was extracted thrice with $CHCl_3$ (80 mL each). The combined $CHCl_3$ extracts were washed thrice with 1M NaOH (100 mL each), twice with $H_2O$ (200 mL each) and finally with brine (150 mL). The solution was then dried over $MgSO_4$, filtered and evaporated to dryness in vacuo to afford 4-(tetra-O-acetyl-$\beta$-D-galactopyranosyloxy)-benzaldehyde (9.33 g; 82%) as a yellow foam used without further purification. [Identical to that prepared by H-R. Rackwitz, Carbohydrate Research, 88:223-32(1981)]

IR (KBr) $cm^{-1}$: 1740, 1685, 1595, 1362, 1218, 1063

$^1$H NMR ($CDCl_3$)$\delta$: 2.03 (s, 3H), 2.04 (s, 3H), 2.10 (s, 3H), 2.20 (s, 3H), 4.21 (br. s, 3H), 5.03-5.63 (m, 4H), 7.06-7.95 (AB, 4H), 9.93 (s, 1H).

A solution of 4-(tetra-O-acetyl-$\beta$-D-galactopyranosyloxy)-benzaldehyde (9.33 g; 20.6 mmol) in absolute methanol (250 mL) was treated with sodium methoxide (90 mg) and allowed to stir for 2 hours at ambient temperature. The reaction was then neutralized by addition of glacial acetic acid (about 0.2 mL) and evaporated to dryness under reduced pressure. The crude product was crystallized from hot EtOH (250 mL) to give (4) (4.45 g; 75.9%) as fine yellow needles with mp=189°-92° C. [mp=155-7° C., Z. Csuros et al., Acta. Chim. Acad. Sci. Hung., 42(3), 263-7(1964); mp=177° C., F. Konishi et al., Agric. Biol. Chem., 47(7), 1419(1983)] The mother liquor was worked for a second crop (0.46 g; 7.8%).

IR (KBr) $cm^{-1}$: 3350, 1685, 1600, 1515, 1250, 1090.

$^1$H NMR (DMSO-$d_6$)$\delta$: 3.40-3.85 (m, 6H), 4.65 (v.v.br. s, 4H), 5.01 (d, J=7Hz, 1H), 7.10-7.95 (AB, 4H), 9.89 (s, 1H);

$^{13}$C NMR (DMSO-$d_6$)ppm: 191.44, 162,38, 131.68, 130.64, 116.60, 100.60, 75.82, 73.42, 70.42, 68.34, 60.60.

4-($\beta$-D-Galactopyranosyloxy)-1-naphthaldehyde (5)—A solution of 4-hydroxynaphthaldehyde (2) (Trans World Chemical Co., Rockville, Md., U.S.A.) (4.304 g, 25 mmol) in aqueous 1.0M NaOH (25 mL) was treated with a solution of acetobromo-$\alpha$-D-galactose (5.14 g, 12.5 mmol) in acetone (100 mL). The reaction mixture was stirred at ambient temperature for 21.5 hours then the acetone was removed under reduced pressure. The resulting dark mixture was extracted four times with CHCl₃ (40 mL each) then the combined CHCl₃ layers were washed thrice with aqueous 1.0M NaOH (50 mL each), twice with H₂O (50 mL each) and once with brine (50 mL). The CHCl₃ solution was then dried over MgSO₄, filtered and evaporated to dryness in vacuo to give crude product as a beige foam (4.02 g). One crystallization from EtOAc/hexane afforded 4-(tetra-O-acetyl-β-D-galactopyranosyloxy)-1-naphthaldehyde (2.79 gm, 44.4%) as analytically pure white rods with mp=177°–8° C.

Analysis: Calculated for $C_{25}H_{26}O_{11}$: C, 59.76; H, 5.22. Found: C, 59.39; H, 5.25.

IR (KBr) cm⁻¹: 1740, 1682, 1600, 1572, 1510, 1368, 1220, 1060, 770.

¹H NMR (DMSO-d₆)δ: 2.00 (s, 3H); 2.03 (s, 3H); 2.05 (s, 3H); 2.18 (s, 3H); 4.20 (d, J=6 Hz, 2H); 4.65 (t, J=6 Hz, 1H); 5.48 (br. s, 3H); 5.90 (br. d, J=6 Hz, 1H); 7.37 (d, J=8 Hz, 2H); 7.55-7.90 (m, 2H); 8.00-8.35 (m, 2H); 9.12-9.35 (m, 1H); 10.28 (s, 1H).

¹³C NMR (DMSO-d₆)ppm: 192.68, 169.92, 169.79, 169.46, 156.72, 138.64, 131.23, 129.60, 126.94, 126.02, 124.66, 124.27, 121.47, 107.56, 97.61, 70.94, 69.90, 68.34, 67.24, 61.32, 20.29 (4 coincident bands).

A solution of 4-(tetra-O-acetyl-β-D-galactopyranosyloxy)-1-naphthaldehyde (1.67 g; 3.32 mmol) in HPLC-grade methanol (40 mL) was heated in a 60° C. bath and treated with sodium methoxide (15 mg). Within three minutes a thick white solid had separated. After 30 minutes, the reaction was cooled in ice and the solid filtered, washed twice with ice-cold methanol and vacuum dried to give (5) (1.08 g; 97%) as an analytically pure fluffy white solid with no mp<255° C.

Analysis: Calculated for $C_{17}H_{18}O_7$: C, 61.07; H, 5.43. Found: C, 61.10; H, 5.50.

IR (KBr) cm⁻¹: 3400, 1665, 1574, 1513, 1254, 1223, 1100, 768.

¹H NMR (DMSO-d₆)δ: 3.44-3.64 (m, 3H); 3.68-3.88 (m, 3H); 4.60 (d, J=4.6 Hz, 1H); 4.69 (t, J=5.5 Hz, 1H); 4.96 (d, J=5.7 Hz, 1H); 5.19 (d, J=7.7 Hz, 1H); 5.41 (d, J=5.4 Hz, 1H); 7.35 (d, J=8.2 Hz, 1H); 7.61-7.67 (m, 1H); 7.72-7.78 (m, 1H); 8.14 (d, J=8.2 Hz, 1H); 8.44 (d, J=7.8 Hz, 1H); 9.20 (d, J=8.1 Hz, 1H); 10.21 (s, 1H).

¹³C NMR (DMSO-d₆)ppm: 192.59, 158.09, 139.14, 131.17, 129.30, 126.25, 125.08, 125.03, 123.95, 122.68, 107.61, 101.00, 75.89, 73.16, 70.32, 68.17, 60.42.

6-(β-D-Galactopyranosyloxy)-2-naphthaldehyde (6)—Under argon, 6-hydroxy-2-naphthaldehyde (3) [R. Gandhi, J. Chem. Soc., 2530 (1955)] (4.4 g, 25.6 mmole) was dissolved in 100 mL of quinoline to give a light yellow solution. Then acetobromo-α-D-galactose (21.05 g, 51.2 mmole) and silver (I) oxide (12.8 g, 55 mmole) were added and the resulting reaction mixture was stirred at room temperature under dark for 22 hours. The reaction mixture was filtered and the filter-cake was washed with EtOAc thoroughly. The dark reddish brown filtrate was then washed with 1.25N HCl until the washing was very acidic. The acidic aqueous solution was then extracted with EtOAc. The EtOAc solutions were combined and washed with 5% NaHCO₃ and saturated NaCl solutions, dried over anhydrous MgSO₄, filtered and concentrated to give a brown viscous material which was dissolved in CHCl₃ and flash-chromatographed with 500 mL silica gel eluted with CH₂Cl₂/CH₃OH (10/0.1, v/v) to give about 13 g of 6-(tetra-O-acetyl-β-D-galactopyranosyloxy)-2-naphthaldehyde as an off-white solid.

Under argon, 6-(tetra-O-acetyl-β-D-galactopyranosyloxy)-2-naphthaldehyde obtained above (12.8 g, 25.5 mmole) was dissolved in 100 mL of methanol and sodium methoxide (1 g, 18.5 mmole) was added. The resulting reaction mixture was heated in a 60° C. oil bath for one-half hour. The reaction mixture was allowed to be adsorbed onto 60 mL of silica gel while being concentrated and then flash-chromatographed with 800 mL of silica gel eluted with CH₂Cl₂/CH₃OH (8.5/1.5, v/v) to give an off-white solid. Recrystallization from absolute ethanol yielded 6.7 g (78.8%) of a white solid (6) mp=193° C. (dec.) .

Analysis: Calculated for $C_{17}H_{18}O_7 \cdot 1/10\ H_2O$: C, 60.75; H, 5.46. Found: C, 60.60; H, 5.63.

IR (KBr) cm⁻¹: 3403, 1681, 1624, 1477, 1267, 1182, 1071, 781.

¹H NMR (DMSO-d₆)δ: 3.42-3.59 (m, 3H); 3.61-3.78 (m, 3H); 4.55 (d, J=5, 1H); 4.68 (t, J=5, 1H); 4.90 (d, J=5, 1H); 7.38 (dd, J=9, J=2, 1H); 7.57 (d, J=2, 1H); 7.85 (d, J=8.6, 1H); 7.92 (d, J=8.6, 1H); 8.11 (d, J=9, 1H); 8.51 (s, 1H); 10.09 (s, 1H).

¹³C NMR (DMSO-d₆)ppm: 60.39, 68.16, 70.31, 73,37, 75.69, 100.91, 110.61, 119.90, 122,92, 127.91, 128.03, 131.20, 132.34, 134.18, 137.41, 157,84, 192.45.

B. Preparation of Substrate Compounds by Convergent Synthesis

1-Ethyl-2-(4'-β-D-galactopyranosyloxystyryl)-3, 3-dimethylindolenium iodide (16)—A mixture of 4-(β-D-galactopyranosyloxy)-benzaldehyde (4) (1 g, 3.5 mmole), 2,3,3-trimethylindolenine ethiodide (7) [H. Richter & R. L. Dresser, J. Chem. Eng. Data, 9(3), 406-7 (1964)] (1.1 g, 3.5 mmole) and 20 mL of anhydrous pyridine was heated in a 65° C. oil bath to give a dark orange solution. After four hours of reaction, yellow solid separated out. The pyridine was evaporated off under reduced pressure. The solid was dissolved in hot methanol, adsorbed onto 10 mL of silica gel while concentrating the solution, then flash-chromatographed with 300 mL of silica gel eluted with CH₂Cl₂/CH₃OH (8.5/1.5, v/v) to give 800 mg (40%) of substrate (16) mp 139° C. (dec.)

IR (KBr) cm⁻¹: 3372, 1588, 1525, 1480, 1246, 1174, 1071, 768.

¹H NMR (DMSO-d₆)δ: 1.45 (t, J=5, 3H); 1.8 (s, 6H); 3.38-3.60 (m, 3H); 3.65-3.74 (m, 3H); 4.56 (d, J=4.6, 1H); 4.67 (m, 3H); 4.92 (d, J=5.7, 1H); 7.21 (d, J=9, 2H); 7.60 (m, 3H); 7.89 (m, 2H); 8.24 (d, J=9, 2H); 8.44 (d, J=16, 1H).

¹³C NMR (DMSO-d₆)ppm: 13.69, 25.78, 52.11, 60.39, 68.14, 70.20, 73.29, 75.77, 100.29, 110.27, 114.90, 116.79, 123.10, 128.19, 129.14, 133.05, 140.42, 143.53, 143.78, 153.86, 161.85, 181.28.

MS(FAB, glycerol/methanol), m/z (rel int): 454 (M⁺, 21.9%); 292 (M⁺—162, 100%).

1-Ethyl-2-(4'-β-D-galactopyranosyloxynaphthyl-1-vinylene)-3,3-dimethylindolinium iodide (17)—A stirred mixture of 4-(β-D-galactopyranosyloxy)-1-naphthaldehyde (5) (5.95 g; 17.8 mmol) and molecular seive 4 Å (15 g) in anhydrous pyridine (105 mL) was maintained at 65°–8° C. under an inert gas atmosphere. This was treated every 45 minutes for 2.25 hours with 1.68 g portions of 2,3,3-trimethylindoleninium ethiodide (7) (H. Richter & R. L. Dresser, supra) (6.72 g total; 21.3 mmol) then allowed to stir for 2 hours. The reaction was cooled, filtered and evaporated to dryness in vacuo. The residue was chromatographed on silica gel (475 g) developed with dichloromethane/methanol (85:15, v/v) solvent and fractions containing (18) were pooled and evaporated to dryness in vacuo. The crude product was dissolved at ambient temperature in methanol (100 mL), diluted with ethyl acetate (700 mL) and cooled at 0° C. overnight. The solid which separated was collected by filtration, washed with ethyl acetate and vacuum dried to give (17) (3.15 g). One recrystallization, as above, from methanol (75 mL) and ethyl acetate (600 mL) afforded analytically pure (17) (2.65 g; 24%) as a red solid with mp=165° C. (dec.).

IR (KBr) cm$^{-1}$: 3320, 1562, 1509, 1268, 1225, 1078, 762.

$^1$HMR (DMF-d$_7$)δ: 1.62 (t, J=7, 3H); 2.00 (s, 6H); 3.47 (v br. s, 4H); 3.56–3.84 (m, 3H); 3,87–4.12 (m, 3H); 4.98 (q, J=7, 2H); 5.37 (d, J=7.7, 1H); 7.52 (d, J=8.5, 1H); 7.71 (m, 3H); 7.84 (t, J=7Hz, 1H); 7.95–8.12 (m, 3H); 8.56 (t, J=7, 2H); 8.75 (d, J-8.5, 1H); 9.21 (d, J=16. 1H).

$^{13}$C NMR (DMF-d$_7$)ppm: 13.99, 26.73, 43.18, 53.14, 61.59, 69.23, 71.67, 74.54, 77.03, 102.17, 109.80, 112.76, 115.64, 123.45, 123.76, 123.96, 125.07, 126.81, 129.47, 129.86, 129.91, 131.26, 133.62, 141.48, 144.66, 150.10, 159.37, 181.8.

| | |
|---|---|
| MS (FAB, glycerol/ methanol) m/z (rel int): | 504 (M$^+$, 4.5%) 342 (M-162, 100%) 127 (I$^+$, 95%). |

Analysis: calculated for C$_{30}$H$_{34}$INO$_6$.H$_2$O: C, 55.47; H, 5.59; N, 2.16. Found: C, 55.31; H, 5.55; N, 2.02.

1-Ethyl-2-(6'-β-D-galactopyranosyloxynaphthyl-2'-vinylene)-3,3-dimethylindolenium iodide (18)—Under argon, a mixture of 6-(β-D-galactopyranosyloxy)-2-naphthaldehyde, (6) (2.23 g, 6.7 mmole), 2,3,3-trimethylindolenine ethiodide (7) (H. Richter & R. L. Dresser, supra) (2.1 g, 6.7 mmole) and 40 mL of anhydrous pyridine was heated in a 70° C. oil bath for 21 hours. Then pyridine was evaporated off under reduced pressure to give a viscous dark reddish brown residue which was dissolved in CH$_2$Cl$_2$/CH$_3$OH (9/1, v/v) and flash-chromatographed with 450 mL silica gel and eluted with CH$_2$Cl$_2$/CH$_3$OH (9:1, v/v) to give 2 g (48%) of substrate (18) as a red solid. mp 177° C. (dec.)

IR(KBr) cm$^{-1}$: 3400, 1587, 1470, 1310, 1189, 1072, 760.

$^1$H NMR (DMSO-d$_6$)δ: 1.48 (t, J=5, 3H); 1.85 (s, 6H); 3.43–3.59 (m, 3H); 3.61–3.77 (m, 3H); 4.57 (d, J=4.5, 1H); 4.69 (t, J=5.5, 1H); 4.76 (q, J=7, 2H); 4.92 (d, J=5.7, 1H); 5.08 (d, J=7.7, 1H); 5.26 (d, J=5.1, 1H); 7.38 (dd, J=9, J=2.4, 1H); 7.58 (d, J=2.2, 1H); 7.64 (m, 2H); 7.76 (d, J=16, 1H), 7.89–8.03 (m, 4H); 8.37 (dd, J=9, J=1.4, 1H); 8.61 (d, J=16, 1H); 8.73 (s, 1H).

$^{13}$C NMR (DMSO-d$_6$) ppm: 13.35, 25.49, 42.00, 52.09, 60,30, 68.02, 70.24, 73.27, 75.57, 100.93, 110.84, 111.29, 114.77, 119.85, 122,76, 124.68, 127.71, 128.37, 128.86, 129.12, 130.12, 130.79, 134.04, 136.57, 140.15, 143.64, 154.04, 157.85, 181.33.

MS(FAB, glycerol) m/z (rel int): 504 (M$^+$, 10%); 342 (M-162, 45%).

MS (EI) m/z: 127 (I$^+$, 90%).

3-Ethyl-2-(4'-β-D-galactopyranosyloxystyryl) benzothiazolium chloride (19)—A solution of (4) (0.284 g; 1 mmol) and 2-methylbenzothiazole ethiodide (8) (H. Richter & R. L. Dresser, supra) (0.336 g; 1.1 mmol) in anhydrous pyridine (5 mL) was heated in a 75° C. bath for about 20 hours, then cooled to ambient temperature and evaporated to dryness under reduced pressure. The dark purple residue was diluted with a minimal volume of methanol and loaded onto a 1⅛" diameter×11" long low pressure C-18 reverse phase column (Bondapak Prep C-18 packing, Waters Division, Millipore Corp., Milford, Mass., U.S.A.) previously equilibrated and developed with 0.75M NaCl/MeOH (7:3, v/v). Fractions containing the yellow product were identified by incubating aliquots with β-galactosidase in pH=8 phosphate buffer. These were pooled, evaporated to dryness in vacuo and de-salted by repeated methanol extractions leaving a yellow solid (0.47 g). This was further purified by twice passing the material through a 1⅛"×33" Sephadex LH-20 column (Pharmacia LKB Biotechnology Inc., Piscatway, N.J., U.S.A.) packed and developed with methanol. As before, fractions containing the desired product were identified by incubating aliquots with β-galactosidase in pH=8 phosphate buffer then pooled and evaporated to dryness in vacuo at ambient temperature for two days to afford (19) (0.14 g; 29%) as an orange solid. HPLC analysis on a single Waters μ-bondapak C-18 column (Waters Division, Millipore Corp., Milford, Mass., U.S.A.) using CH$_3$CN/0.01M NaH$_2$PO$_4$ (1:4, v/v) solvent flowing at 1.0 mL/minute and either 254 nm or 410 nm detection revealed only one band with t$_R$=9.9 minutes.

IR (KBr) cm$^{-1}$: 3360, 1595, 1510, 1227, 1180, 1070.

$^1$H NMR (DMSO-d$_6$)δ: 1.45 (br. t, J=8 Hz, 3H), 3.10–3.85 (m, 7H), 4.55–5.30 (m, 6H), 7.18 (d, J=8 Hz, 2H), 7.65–8.55 (m, 8H).

$^{13}$C NMR (DMSO-d$_6$) ppm: 171.61, 168.16, 160.88, 145.11, 140.79, 132.01, 129,41, 128.11, 127.65, 124.40, 116.66, 116.42, 111.20, 100.40, 75.69, 73.41, 70.29, 67.85, 60.21, 44.14, 14.11.

3-Ethyl-2-(4'-β-D-galactopyranosyloxynaphthyl-1'-vinylene)-benzothiazolium iodide (20)—Approximately equal amounts of 4-(β-D-galactopyranosyloxy) -1-naphthaldehyde (5) and 2-methylbenzothiazole ethiodide (8) (H. Richter & R. L. Dresser, supra) were heated at reflux for about 1 minute in ethanol containing a small amount of piperidine. The initially colorless mixture became red-orange during this time. The presence of (20) in the reaction mixture was determined by mixing a portion of the reaction mixture with an equal amount of dimethylformamide, diluting this with 0.1M phosphate buffer pH=7.0, and then treating the resulting solution with β-galactosidase. When the enzyme was added the solution turned from yellow in color to violet.

3-Ethyl-2-(4'-β-D-galactopyranosyloxynaphthyl-1'-vinylene)-6-methoxybenzothiazolium iodide (21)—Under argon, 6-methoxy-2-methylbenzothiazole (5 g, 27.9 mmole, Aldrich Chemical Company, Inc., Milwaukee, Wis., U.S.A.) and ethyliodide (5.4 mL, 67 mmole, Aldrich Chemical Company, Inc., Milwaukee, Wis., U.S.A.) were mixed and heated in a 60° C. oil bath for about 20 hours. The solid separated out was filtered, washed thoroughly with acetone and dried to give a white solid of 6-methoxy-2-methylbenzothiazole ethiodide (9) (2 g, 21%), mp=180°-182° C.

IR (KBr) cm$^{-1}$: 2968, 1601, 1481, 1443, 1251, 1048, 853, 814.

$^1$H NMR (DMSO-d$_6$)δ: 1.50 (t, J=7Hz, 3H), 3.25 (s, 3H), 3.95 (s, 3H) 4,80 (q, J=7 Hz 2H), 7.40-8.50 (m, 3H).

MS (FAB, glycerol/methanol) m/z (rel int); 308 (M$^+$, 100%).

Analysis: calculated for C$_{11}$H$_{14}$INOS: C, 39.42; H, 4.21; N, 4.18. Found: C, 39.62; H, 4.21; N, 4.34.

Under argon, a mixture of 4-(β-D-galactopyranosyloxy)naphthaldehyde (5) (0.5 g, 1.5 mmole), 6-methoxy-2-methylbenzothiazole ethiodide (9) (0.75 g, 2.3 mmole) and 10 mL of anhydrous pyridine is heated at 65° C. oil bath. Orange solid separated out from the reaction mixture gradually. After five hours of reaction, the reaction mixture was cooled to room temperature, filtered, and the solid washed with pyridine, $CHCl_3$ and $CH_3OH$ to give a bright orange solid. After drying under reduced pressure at room temperature overnight yielded 0.5 g (50%) of substrate (21), mp 229° C. (dec.).

Analysis: Calculated for $C_{28}H_{30}INO_7S$: C, 51.62; H, 4.64; N, 2.15. Found: C, 51.38; H, 4.53; N, 2.30.

IR (KBr)cm$^{-1}$: 3380, 1603, 1566, 1253, 1227, 1079, 770.

$^1H$ NMR (DMSO-$d_6$)δ: 1.48 (t, J=7, 3H); 3.48-3.64 (m, 3H); 3.71-3.87 (m, 3H); 3.95 (s, 3H); 4.62 (d, J=5, 1H); 4.70 (t, J=5, 1H); 4.88-5.02 (m, 3H); 5.18 (d, J=7.6, 1H); 5.44 (d, J=5, 1H); 7.37 (d, J=8.5, 1H); 7.46 (dd, J=7.1, J=2.2, 1H); 7.65 (t, J=7.6, 1H); 7.76 (t, J=7.0, 1H); 8.02 (m, 2H); 8.21 (d, J=9.3, 1H); 8.47 (m, 3H); 8.78 (d, J=15.5, 1H).

$^{13}C$ NMR (DMSO-$d_6$)ppm: 13.36, 43.68, 55.51, 59.68, 67.38, 69.48, 72.30, 75.11, 100.26, 105.95, 107.97, 112.01, 116.63, 117.75, 122.11, 123.04, 124.15, 125.08, 127.30, 128.12, 129.26, 131.19, 134.09, 142.77, 156.29, 158.51, 167.59.

MS(FAB, glycerol/methanol/HCl) m/z (rel int): 362-(M-162, 12%).

MS(EI) m/z (rel int): 127 (I+, 100%).

2-(4'-β-D-galactopyranosyloxynaphthyl-1'-vinylene)-3-methyl-β-naphthothiazolium iodide (22)—Under argon, a mixture of 4-(β-D-galactopyranosyloxy)naphthaldehyde (5) (0.50 g, 1.5 mmole), 2-methyl-β-naphthothiazole methiodide (10) (H. Richter & R. L. Dresser, supra) (0.61 g, 1.8 mmole), 20 mL of anhydrous pyridine and 10 mL of anhydrous DMF was heated in a 65° C. oil bath for five hours to give a dark brownish red mixture. Thin-layer chromatography (TLC) showed the presence of large amounts of aldehyde starting material. Another portion of 2-methyl-β-naphthothiazole methiodide (10) (0.61 g, 1.8 mmole) was added to the reaction mixture. After an additional two hours of reaction, the reaction mixture was filtered and pyridine and DMF were evaporated off under reduced pressure. About 1 mL of KI in methanol solution (1 g KI/8 mL methanol) was added to the residue and the mixture was then adsorbed onto 10 mL of silica gel while the methanol was being evaporated off under reduced pressure. Flash-chromatography with 200 mL of silica gel eluted with $CH_2Cl_2/CH_3OH$ (8.5/1.5, v/v) followed by recrystallization from $CH_3OH/Et_2O$ yielded 27 mg (3%) of substrate (22) as a red solid, mp 160° C.

IR (KBr) cm$^{-1}$: 3440, 1620, 1564, 1230, 1076, 775.

$^1H$ NMR (DMSO-$d_6$)δ: 3.40-3.68 (m, 3H); 3.72-3.90 (m, 3H); 4.63 (d, J=5, 1H); 4.72 (t, J=5, 1H); 4.82 (s, 3H); 4.98 (d, J=5, 1H); 5.19 (d, J=7.7, 1H); 5.44 (d, J=5, 1H); 7.38 (d, J=8.6, 1H); 7.64 (m, 1H); 7.76 (m, 1H); 7.89 (m, 2H); 8.15 (m, 1H); 8.33 (d, J=9, 2H); 8.43 (m, 2H); 8.52 (d, J=8.6, 2H); 8.83 (d, J=15, 1H); 9.00 (d, J=7.7, 1H).

$^{13}C$ NMR (DMSO-$d_6$)ppm: 42.0, 60.36, 68.18, 70.37, 73.16, 75.87, 100.91, 107.57, 108.85, 113.79, 119.63, 122.75, 122.93, 124.04, 124.95, 125.91, 127.85, 128.09, 128.52, 128.73, 129.92, 131.13, 132.08, 133.58, 137.85, 139,28, 143.15, 145.41, 156.53, 170.15.

3-Ethyl-2-(4'-β-D-galactopyranosyloxynaphthyl-1'-vinylene)-5-methylbenzothiazolium iodide (23) Under argon, 2,5-dimethylbenzothiazole (10 g, 61 mmole, Aldrich Chemical Company, Inc., Milwaukee, Wis.) and ethyliodide (9.8 mL, 123 mmole, Aldrich Chemical Company, Inc., Milwaukee, Wis.) were mixed and heated in a 65° C. oil bath for about 23 hours. The solid separated out was filtered, washed thoroughly with acetone, recrystallized from absolute ethanol and dried to give a white solid of 2,5-dimethylbenzothiazole ethiodide (11) (3 g, 15.4%), mp-202°-3° C.

Analysis: calculated for $C_{11}H_{14}INS$: C, 41.39; H, 4.42; N, 4.39. Found: C, 41.71; H, 4.44; N, 4.50.

A mixture of 4-(β-D-galactopyranosyloxy)-naphthaldehyde (5) (0.33 g, 1 mmole), 2,5-dimethylthiazole ethiodide (11) (0.38 g, 1.2 mmole), 3 mL of pyridine and some molecular sieves was heated in a 120° C. oil bath in a closed flask for 7 minutes. Then the reaction mixture was cooled and 30 ml of acetone was added. The red solid separated out was filtered and washed with acetone. The solid was then dissolved in pyridine and purified with silica gel column eluted with $CH_2Cl_2/CH_3OH$ (3/7, v/v) to give 0.2 g of substrate (23) as a red solid, mp 160° C. (dec.).

MS(FAB, diethiothreitol/dithioerythritol/methanol) m/z: 508 (M+, 2.3%) 346 (M-162, 30.1%).

3-Ethyl-2-(6'-β-D-galactopyranosyloxynaphthyl-2'-vinylene)-benzoselenazolium iodide (24)—A mixture of 6-(β-D-galactopyranosyloxy)-2-naphthaldehyde (6) (34 mg, 0.1 mmole), 2-methylbenzoselenazole ethiodide (12) (H. Richter & R. L. Dresser, supra) (35 mg, 0.1 mmole) and 0.5 mL of anhydrous pyridine was heated in a 70° C. oil bath for 20 hours. TLC analysis with solvent $CH_2Cl_2/CH_3OH$ (8.5/1.5, v/v) showed the presence of a yellow product spot which was extracted with 0.3M bicene buffer (pH 7.9). On addition of β-galactosidase and a drop of 1N NaOH, the solution turned to purple immediately.

3-(2''-Carboxyethyl)-2-(4'-β-D-galactopyranosyloxynaphthyl-1'-vinylene)-5-methyl benzoxazolium bromide, (25)—Under argon, a mixture of 4-(β-D-galactopyranosyloxy)-naphthaldehyde (5) (0.5 g, 1.5 mmole), 3-(2'-carboxyethyl)-2,5-dimethylbenzoxazolium bromide (13) (Aldrich Chemical Company, Inc.) (1.35 g, 4.5 mmole) and 10 mL of anhydrous pyridine was heated in a 65° C. oil bath for 3½ hours. The reaction mixture was then cooled to room temperature and then flash-chromatographed with 80 mL of silica gel eluted with $CH_2Cl_2/CH_3OH$ (8.5/1.5, v/v) to give 240 mg (30%) of substrate (25) as a red solid, mp 150° C. (dec.).

IR (KBr) cm$^{-1}$: 3219, 1730, 1606, 1567, 1512, 1270, 1224, 1077, 770.

$^{13}C$ NMR (DMSO-$d_6$)δ: 20.0, 32.5, 44.07, 60.41, 68.16, 70.41, 73.26, 75.73, 101.49, 108.87, 116.50, 122.80, 124.02, 125.27, 125.49, 127.24, 127.73, 128.14, 129.77, 131.58, 136.79, 137.21, 139.38, 142.06, 145.21, 151.07, 154.20, 165.20, 172.04.

MS (FAB, glycerol/methanol/HCL) m/z 536 (M+, 4%), 374 (M-162, (rel int): 20%).

1-Ethyl-2-(4'-β-D-galactopyranosyloxynaphthyl-1'-vinylene)-quinolinium iodide (26)—A mixture of 4-(β-D-galactopyranosyloxy)-naphthaldehyde (5) (0.33 g, 1 mmole), quinaldine ethiodide (14) (H. Richter & R. L. Dresser, supra) (0.30 g, 1 mmole), some molecular sieve (4 Å, 8-12 mesh) and 5 mL of anhydrous pyridine in a stoppered round-bottomed flask was heated in a 120° C. oil bath for 15 minutes. Thin-layer chromatography showed the presence of large amounts of aldehyde starting material. An additional portion of quinaldine ethiodide (0.1 g, 0.3 mmole) was added and the resulting reaction mixture was heated for an additional ten minutes to give a dark viscous mixture. Then the reaction mixture was cooled, acetone was added and the resulting slurry was filtered and washed with large amount of acetone to give a bright orange solid. The orange crude product was dissolved in warm DMSO and was then flash-chromatographed with 90 mL of silica gel eluted with $CH_2Cl_2/CH_3OH$ (9/1, v/v). Orange solid crystallized out from the fractions containing the product and was filtered and dried under reduced pressure at room temperature overnight to yield 26 mg (4%) of substrate (26) as a bright orange solid. mp 236°–237° C. (dec.).

IR (KBr) cm$^{-1}$: 3367, 1603, 1568, 1339, 1219, 1076, 760.

$^1$H NMR (DMSO-d$_6$)δ: 1.60 (t, J=7, 3H); 3.46–3.67 (m, 3H); 3.70–3.90 (m, 3H); 4.62 (d, J=4.5, 1H); 4.71 (t, J=5.1, 1H); 4.97 (d, J=5.6, 1H); 5.17 (m, 3H); 5.43 (d, J=5.2, 1H); 7.37 (d, J=8.5, 1H); 7.63 (t, J=7.5, 1H); 7.73 (t, J=7.5, 1H); 7.86 (d, J=15.5, 1H); 7.94 (t, J=7.3, 1H); 8.19 (t, J=7.8, 1H); 8.33–8.51 (m, 3H); 8.57 (d, J=9.0, 1H); 8.63 (d, J=8.6, 1H); 8.90 (d, J=9.0, 1H); 9.00 (d, J=15.2, 1H); 9.06 (d, J=9, 1H).

$^{13}$C NMR (DMSO-d$_6$)ppm: 12.51, 47.15, 61.91, 70.12, 72.37, 75.36, 78.32, 105.22, 113.35, 123.40, 124.04, 127.10, 128.30, 128.86, 130.49, 130.63, 131.52, 133.60, 133.79, 133.87, 134.68, 136.26, 138.33, 141.25, 144.45, 150.34, 150.70, 162.70, 163.71.

| MS (FAB, dithiothrietol/ dithioerythritol/ methanol)m/z (rel int): | 488 (M$^+$, 7.7%); 326 (M-162, 100%) |
| --- | --- |
| MS(EI) m/z (rel int): | 127 (I$^+$, 30%). |

1-Ethyl-2-(4'-β-D-galactopyranosyloxynaphthyl-1'-vinylene)-6-methoxyquinolinium iodide (27)—Under argon, 6-methoxyquinaldine (10 g, 58 mmole, Aldrich Chemical Company, Inc., Milwaukee, Wis., U.S.A.) and ethyliodide (9.3 mL, 116 mmole) were mixed and heated in a 65° C. oil bath for about 20 hours. Acetone was added to the reaction mixture. The solid was filtered, washed thoroughly with acetone, recrystallized from absolute ethanol and dried to give a light yellow solid of 6-methoxyquinaldine ethiodide (15) (4.2 g, 22%).

A mixture of 4-(β-D-galactopyranosyloxy)naphthaldehyde (5) (0.3 g, 0.9 mmole), 6-methoxyquinaldine ethiodide (15) (0.36 g, 1.1 mmole), some molecular sieve (3 Å, 8–12 mesh) and 2 ml of anhydrous pyridine was heated in a 120° C. oil bath for 10 minutes. DMF was added and the resulting reaction mixture was then flash-chromatographed with 90 mL of silica gel eluted with $CH_2Cl_2/CH_3OH$ (8/2, v/v) to give 26 mg of a red solid of substrate (27) (6%). MS(FAB, dithiothreitol/dithioerythritol/methanol) m/z: 518 (M$^+$, 7.1%); 356 (M$^+$-162, 48.9%)

1-Ethyl-4-(4'-β-D-galactopyranosyloxynaphthyl-1'-vinylene)-quinolinium iodide (29)—A mixture of 4-(β-D-galactopyranosyloxy)-naphthaldehyde (5) (34 mg, 0.1 mmole), lepidine ethiodide (28) (H. Richter & R. L. Dresser, supra) (30 mg, 0.1 mmole) and 0.5 mL of anhydrous pyridine was heated in a 70° C. oil bath for 3 hours. Then an additional of 60 mg of lepidine ethiodide (28), was added and the reaction mixture was allowed to react in the 70° C. oil bath for a total of 20 hours. TLC analysis with solvent $CH_2Cl_2/CH_3OH$ (8/2, v/v) showed the presence of a yellow product spot which was extracted with 50 mM of phosphate buffer (pH 7.4). On addition of β-galactosidase the yellow solution turned to blue color within 5 seconds.

C. Study of Chromogenic Substrate Properties

The properties of some of the compounds were studied and are reported in Table D.

D. Test Strip

The substrates at an indicated concentration in 0.3M Bicene buffer, pH 7.9 and 4 mM $MgCl_2$ were impregnated into Whatman 54 paper (Whatman Inc., Clifton, N.J., U.S.A.) and then air-dried for 1 hour at room temperature. A 0.5×1.0 cm pad of the paper was then mounted onto the end of a 0.5×8.125 cm polystyrene strip (Tricite®, Dow Chemical Co., Midland, Mich., U.S.A.) previously laminated with a 2 mm strip of Double Stick® double-faced adhesive tape (3M Company, St. Paul, Minn., U.S.A.). Thirty microliters of an indicated levels of β-galactosidase in phosphate buffer, pH 7.4, were then added to the substrate pad and reflectances were recorded at five second intervals at the optical absorption maximum of wavelength specified for the chromophore using the SERALYZER® reflectance meter (Miles Inc., Elkhart, Ind., U.S.A.). Reflectance values were linearized through a mathematical function and converted to units identified as L(R) units.

Figure 6:
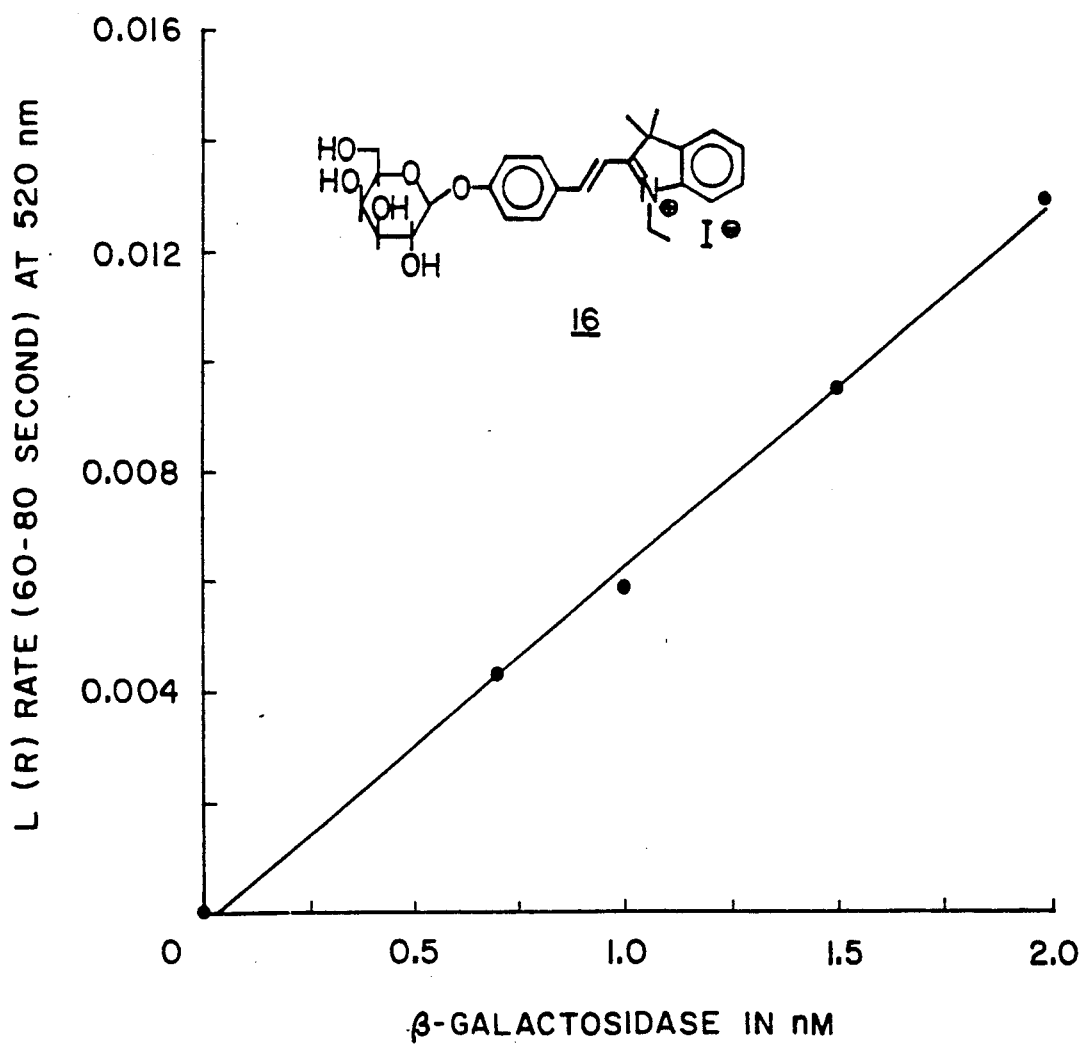
FIGS. 6 through 8 are graphs of the dose response of some substrate compounds of the present invention to the enzyme β-galactosidase.
Figure 7:
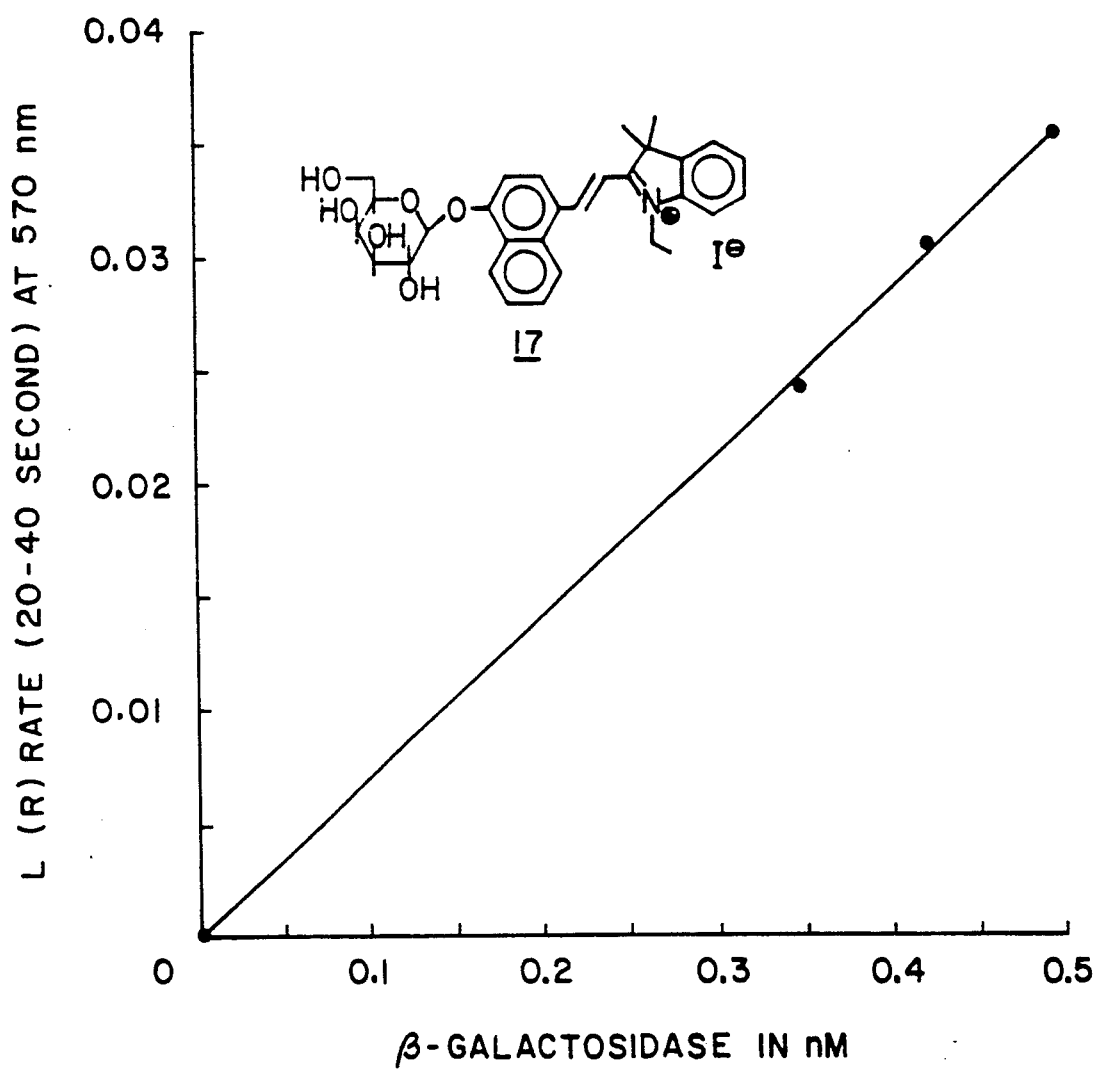
Figure 8:
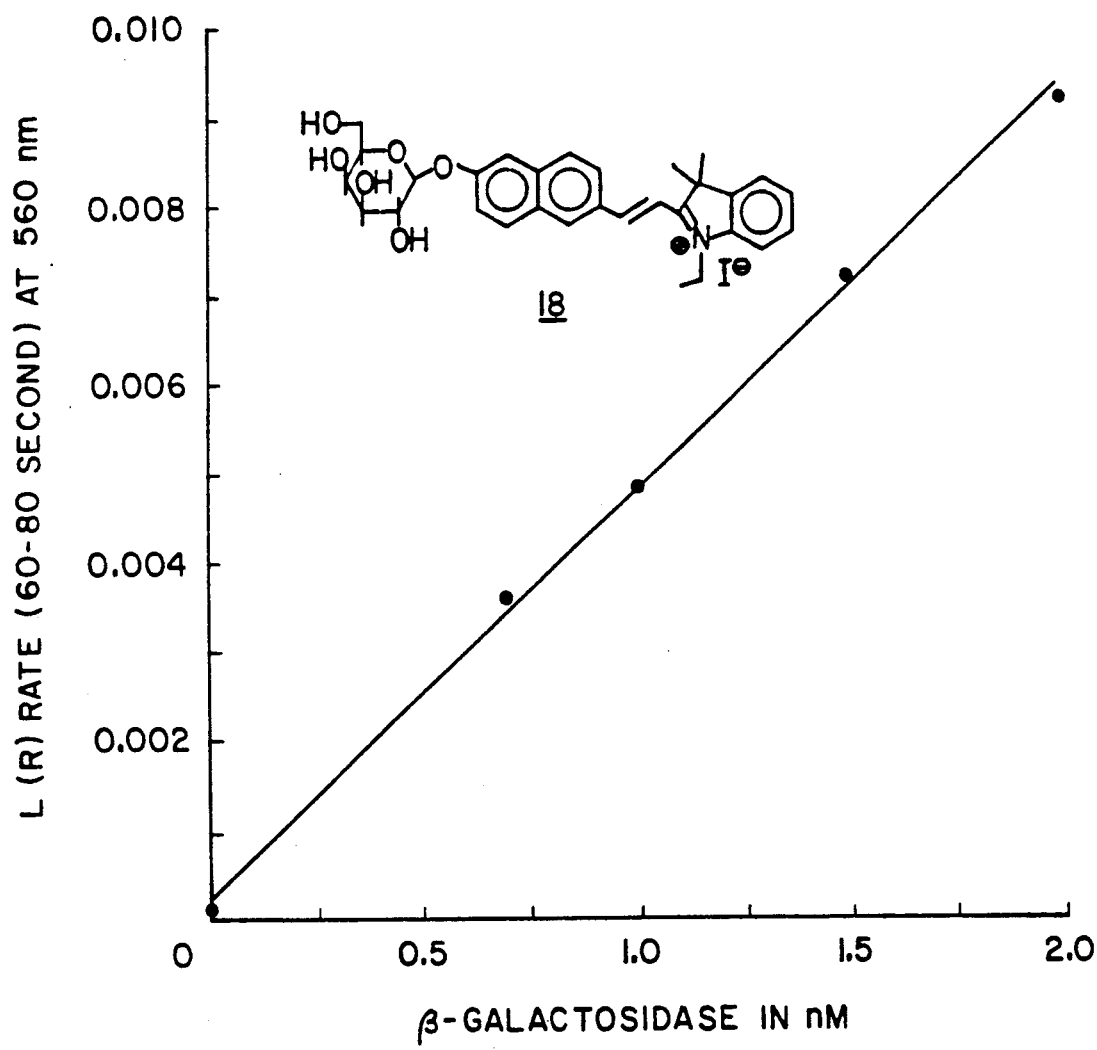

The results were shown in FIGS. 6–8.

The present invention has been particularly described and exemplified above. Obviously, many other variations and modifications of the invention can be made without departing from the spirit and scope thereof.

TABLE D

| | $\lambda_{max}$ | | | $\epsilon \times 10^3$ | | | Km | Kcat mole/min per |
| --- | --- | --- | --- | --- | --- | --- | --- | --- |
| Compound | Substrate | Chromogen | Shift | Substrate | Chromogen | pKa | mM | mole active site |
| 16 | 406 | 522 | 116 | 25.3 | 45.0 | 7.3 | 0.018 | $1.43 \times 10^3$ |
| 17 | 456 | 580 | 124 | 28.0 | 82.0 | 6 | 0.09 | $7.8 \times 10^3$ |
| 18 | 430 | 530 | 100 | 32.2 | — | 8.3 | 0.08 | $1.3 \times 10^4$ |
| 19 | 393 | 492 | 99 | — | 43.0 | 7.6 | 0.017 | $3.04 \times 10^3$ |
| 20 | yellow | violet | — | — | — | — | — | — |
| 21 | 422 | 598 | 176 | 10.5 | 80.1 | 6.6 | 0.43 | $2.8 \times 10^3$ |
| 22 | 470 | 610 | 140 | — | — | 7 | — | — |
| 23 | yellow | blue | — | — | — | — | — | — |
| 24 | yellow | purple | — | — | — | — | — | — |
| 25 | 420 | 550 | 130 | 15.8 | 50.1 | 6.6 | 0.08 | $9.8 \times 10^2$ |
| 26 | 434 | 606 | 172 | 16.0 | 70.2 | 6.5 | — | — |
| 29 | yellow | blue | — | — | — | — | — | — |

What is claimed is:

1. A method for determining a particular enzyme in a liquid test sample, comprising the steps of:
   (a) contacting the test sample with a compound of the formula

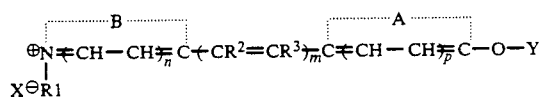

wherein Y is an enzymatically-cleavable group that is (i) capable of being cleaved from such compound by said enzyme or (ii) capable of being modified by said enzyme to produce a secondary substrate compound in which the modified enzymatically-cleavable group is cleavable from the compound by a secondary enzyme, in which case the secondary substrate compound is contacted with said secondary enzyme; A represents a nonmetallic atomic group or residue which completes a 5- or 6-membered carbocyclic or heterocyclic ring or a fused ring system consisting of 5- and/or 6-membered heterocyclic or carbocyclic rings; B represents a nonmetallic atomic group or residue which completes a 5- or 6-membered N-containing heterocyclic ring or a fused ring system consisting of 5- and/or 6-membered heterocyclic or carbocyclic rings; $R^1$ is alkyl or aryl; $R^2$ and $R^3$, which may be the same or different, are hydrogen or lower alkyl; m, n, and p, which may be the same or different, are integers from 0 through 3 provided that m+n+p is at least 2; and X is a counterion (anion); and
   (b) measuring the resulting color generated by the cleaved merocyanine indicator group.

2. The method of claim 1 wherein said enzymatically-cleavable group is a radical of a compound Y-OH selected from the group consisting of sugars and derivatives thereof.

3. The method of claim 2 wherein Y-OH is a sugar or derivative thereof selected from the group consisting of α-D-glucose, α-D-galactose, α-D-glucose, β-D-glucose, α-D-mannose, N-acetylglucosamine and N-acetylneuraminic acid.

4. The method of claim 2 wherein Y-OH is an oligosaccharide chain of from between about 2 to 20 monosaccharide units.

5. The method of claim 2 wherein Y-OH is β-D-galactose, β-D-glucose or α-D-glucose.

6. The method of claim 1 wherein said enzyme-cleavable group is a radical of a compound Y-OH selected from the group consisting of amino acids and peptides.

7. The method of claim 1 wherein said enzyme-cleavable group is phosphate.

8. The method of claim 1 wherein A represents substituted or unsubstituted phenylene, naphthylene or anthrylene.

9. The method of claim 8 wherein A represents 1,2-naphathylene, 1,4-phenylene, 1,4-naphthylene, or 2,6-naphthylene.

10. The method of claim 1 wherein B represents a nonmetallic atomic group or residue which completes a 5- or 6-membered N-containing heterocyclic ring or a fused ring system consisting of three or less 5- and/or 6-membered heterocyclic or carbocyclic rings.

11. The method of claim 10 wherein said residue completes a ring or fused ring system selected from substituted or unsubstituted forms of indolenium, β-naphthothiazolium, benzoxazolium, benzothiazolium, quinolinium, thiazolium, benzoselenazolium, or benzimidazolium.

12. The method of claim 10 wherein said atomic group or residue completes a ring or fused ring system of the formula:

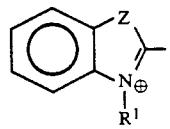

wherein Z is disubstituted methylene, vinylene, alkyl- or aryl-substituted N, O, S or Se, and wherein the phenyl ring in the formula is substituted or unsubstituted.

13. The method of claim 1 wherein $R^1$ is lower alkyl or phenyl.

14. The method of claim 1 wherein $R^2$ and $R^3$ are both hydrogen.

15. The method of claim 1 wherein m+n+p is 3, 4 or 5.